United States Patent
Bertness

(10) Patent No.: US 9,255,955 B2
(45) Date of Patent: Feb. 9, 2016

(54) METHOD AND APPARATUS FOR MEASURING A PARAMETER OF A VEHICLE ELECTRICAL SYSTEM

(75) Inventor: Kevin I. Bertness, Batavia, IL (US)

(73) Assignee: Midtronics, Inc., Willowbrook, IL (US)

( * ) Notice: Subject to any disclaimer, the term of this patent is extended or adjusted under 35 U.S.C. 154(b) by 508 days.

(21) Appl. No.: 13/098,661

(22) Filed: May 2, 2011

(65) Prior Publication Data

US 2011/0265025 A1 Oct. 27, 2011

Related U.S. Application Data

(60) Continuation-in-part of application No. 12/261,336, filed on Oct. 30, 2008, now Pat. No. 8,164,343, which is a continuation-in-part of application No. 11/641,594, filed on Dec. 19, 2006, now Pat. No.

(Continued)

(51) Int. Cl.
*G01N 27/416* (2006.01)
*G01R 31/00* (2006.01)
*G01R 31/02* (2006.01)

(52) U.S. Cl.
CPC ............ *G01R 31/006* (2013.01); *G01N 27/416* (2013.01); *G01R 31/007* (2013.01); *G01R 31/021* (2013.01); *G01R 31/026* (2013.01)

(58) Field of Classification Search
CPC .. G01R 31/006; G01R 31/007; G01R 31/026; G01R 27/416
USPC .......................................................... 324/503
See application file for complete search history.

(56) References Cited

U.S. PATENT DOCUMENTS

| 85,553 A | 1/1869 | Adams ............................ 33/472 |
| 2,000,665 A | 5/1935 | Neal .............................. 439/440 |
| 2,417,940 A | 3/1947 | Lehman ..................... 200/61.25 |
| 2,437,772 A * | 3/1948 | Wall .............................. 324/523 |

(Continued)

FOREIGN PATENT DOCUMENTS

| CN | 2470964 Y | 1/2002 |
| CN | 201063352 Y | 5/2008 |

(Continued)

OTHER PUBLICATIONS

Search Report and Written Opinion from PCT Application No. PCT/US2011/026608, dated Aug. 29, 2011, 9 pgs.

(Continued)

*Primary Examiner* — Jermele M Hollington
*Assistant Examiner* — Christopher McAndrew
(74) *Attorney, Agent, or Firm* — Westman, Champlin & Koehler, P.A.

(57) ABSTRACT

A vehicle electrical system tester for testing the electrical system of a vehicle is provided. The electrical system has a wiring harness which extends between components of the vehicle and includes a plurality of wires. The vehicle electrical system tester is configured to measure an electrical parameter of at least one of the plurality of wires through a first connection to coupled to a first end of the at least one of the plurality of wires and a second connection coupled to a second end of the at least one of the plurality of wires. An electrical signal is applied between the first and second ends of the at least one of the plurality of wires and the electrical parameter of the at least one of the plurality of wires is responsively measured.

32 Claims, 7 Drawing Sheets

Related U.S. Application Data 8,674,711, which is a division of application No. 10/656,526, filed on Sep. 5, 2003, now Pat. No. 7,154,276.

(60) Provisional application No. 61/330,497, filed on May 3, 2010.

(56) References Cited

U.S. PATENT DOCUMENTS

| | | | | |
|---|---|---|---|---|
| 2,514,745 | A | 7/1950 | Dalzell | 324/115 |
| 2,727,221 | A | 12/1955 | Springg | 340/447 |
| 3,025,455 | A | 3/1962 | Jonsson | 323/369 |
| 3,178,686 | A | 4/1965 | Mills | 340/447 |
| 3,215,194 | A | 11/1965 | Sununu et al. | 165/80.3 |
| 3,223,969 | A | 12/1965 | Alexander | 340/447 |
| 3,267,452 | A | 8/1966 | Wolf | 340/249 |
| 3,356,936 | A | 12/1967 | Smith | 324/429 |
| 3,562,634 | A | 2/1971 | Latner | 324/427 |
| 3,593,099 | A | 7/1971 | Scholl | 320/127 |
| 3,607,673 | A | 9/1971 | Seyl | 324/425 |
| 3,652,341 | A | 3/1972 | Halsall et al. | 29/623.2 |
| 3,676,770 | A | 7/1972 | Sharaf et al. | 324/430 |
| 3,699,433 | A * | 10/1972 | Smith, Jr. | 324/523 |
| 3,729,989 | A | 5/1973 | Little | 73/862.192 |
| 3,750,011 | A | 7/1973 | Kreps | 324/430 |
| 3,753,094 | A | 8/1973 | Furuishi et al. | 324/430 |
| 3,776,177 | A | 12/1973 | Bryant et al. | 116/311 |
| 3,796,124 | A | 3/1974 | Crosa | 411/521 |
| 3,808,522 | A | 4/1974 | Sharaf | 324/430 |
| 3,811,089 | A | 5/1974 | Strzelewicz | 324/170 |
| 3,816,805 | A | 6/1974 | Terry | 320/123 |
| 3,850,490 | A | 11/1974 | Zehr | 439/822 |
| 3,857,082 | A * | 12/1974 | van Opijnen | 320/143 |
| 3,873,911 | A | 3/1975 | Champlin | 324/430 |
| 3,876,931 | A | 4/1975 | Godshalk | 324/429 |
| 3,886,426 | A | 5/1975 | Daggett | 320/117 |
| 3,886,443 | A | 5/1975 | Miyakawa et al. | 324/426 |
| 3,889,248 | A | 6/1975 | Ritter | 340/636.11 |
| 3,906,329 | A | 9/1975 | Bader | 320/134 |
| 3,909,708 | A | 9/1975 | Champlin | 324/431 |
| 3,920,284 | A * | 11/1975 | Lane et al. | 303/122.06 |
| 3,936,744 | A | 2/1976 | Perlmutter | 324/772 |
| 3,946,299 | A | 3/1976 | Christianson et al. | 320/430 |
| 3,947,757 | A | 3/1976 | Grube et al. | 324/416 |
| 3,969,667 | A | 7/1976 | McWilliams | 324/427 |
| 3,979,664 | A | 9/1976 | Harris | 324/397 |
| 3,984,762 | A | 10/1976 | Dowgiallo, Jr. | 324/430 |
| 3,984,768 | A | 10/1976 | Staples | 324/712 |
| 3,989,544 | A | 11/1976 | Santo | 429/65 |
| 3,997,830 | A | 12/1976 | Newell et al. | 320/102 |
| 4,008,619 | A | 2/1977 | Alcaide et al. | 73/724 |
| 4,023,882 | A | 5/1977 | Pettersson | 439/426 |
| 4,024,953 | A | 5/1977 | Nailor, III | 206/344 |
| 4,047,091 | A | 9/1977 | Hutchines et al. | 363/59 |
| 4,053,824 | A | 10/1977 | Dupuis et al. | 324/434 |
| 4,056,764 | A | 11/1977 | Endo et al. | 320/101 |
| 4,057,313 | A | 11/1977 | Polizzano | 439/219 |
| 4,070,624 | A | 1/1978 | Taylor | 324/772 |
| 4,086,531 | A | 4/1978 | Bernier | 324/772 |
| 4,106,025 | A | 8/1978 | Katz | 343/715 |
| 4,112,351 | A | 9/1978 | Back et al. | 324/380 |
| 4,114,083 | A | 9/1978 | Benham et al. | 340/636.13 |
| 4,126,874 | A | 11/1978 | Suzuki et al. | 396/301 |
| 4,160,916 | A | 7/1979 | Papasideris | 307/10.6 |
| 4,178,546 | A | 12/1979 | Hulls et al. | 324/772 |
| 4,193,025 | A | 3/1980 | Frailing et al. | 324/427 |
| 4,207,610 | A * | 6/1980 | Gordon | 701/33.9 |
| 4,207,611 | A | 6/1980 | Gordon | 701/33 |
| 4,217,645 | A | 8/1980 | Barry et al. | 702/63 |
| 4,218,745 | A * | 8/1980 | Perkins | 324/66 |
| 4,280,457 | A | 7/1981 | Bloxham | 123/198 R |
| 4,297,639 | A | 10/1981 | Branham | 324/429 |
| 4,307,342 | A * | 12/1981 | Peterson | 324/537 |
| 4,315,204 | A | 2/1982 | Sievers et al. | 322/28 |
| 4,316,185 | A | 2/1982 | Watrous et al. | 340/636.11 |
| 4,322,685 | A | 3/1982 | Frailing et al. | 324/429 |
| 4,351,405 | A | 9/1982 | Fields et al. | 180/65.2 |
| 4,352,067 | A | 9/1982 | Ottone | 324/434 |
| 4,360,780 | A | 11/1982 | Skutch, Jr. | 324/437 |
| 4,361,809 | A | 11/1982 | Bil et al. | 324/426 |
| 4,363,407 | A | 12/1982 | Buckler et al. | 209/3.3 |
| 4,369,407 | A | 1/1983 | Korbell | 324/416 |
| 4,379,989 | A | 4/1983 | Kurz et al. | 320/165 |
| 4,379,990 | A | 4/1983 | Sievers et al. | 322/99 |
| 4,385,269 | A | 5/1983 | Aspinwall et al. | 320/129 |
| 4,390,828 | A | 6/1983 | Converse et al. | 320/153 |
| 4,392,101 | A | 7/1983 | Saar et al. | 320/156 |
| 4,396,880 | A | 8/1983 | Windebank | 320/156 |
| 4,408,157 | A | 10/1983 | Beaubien | 324/712 |
| 4,412,169 | A | 10/1983 | Dell'Orto | 320/123 |
| 4,423,378 | A | 12/1983 | Marino et al. | 324/427 |
| 4,423,379 | A | 12/1983 | Jacobs et al. | 324/429 |
| 4,424,491 | A | 1/1984 | Bobbett et al. | 324/433 |
| 4,425,791 | A | 1/1984 | Kling | 73/116.02 |
| 4,441,359 | A | 4/1984 | Ezoe | 73/116.06 |
| 4,459,548 | A | 7/1984 | Lentz et al. | 324/472 |
| 4,514,694 | A | 4/1985 | Finger | 324/429 |
| 4,520,353 | A | 5/1985 | McAuliffe | 340/636.16 |
| 4,521,498 | A | 6/1985 | Juergens | 429/59 |
| 4,564,798 | A | 1/1986 | Young | 320/103 |
| 4,620,767 | A | 11/1986 | Woolf | 439/217 |
| 4,633,418 | A | 12/1986 | Bishop | 702/63 |
| 4,637,359 | A | 1/1987 | Cook | 123/179 |
| 4,659,977 | A | 4/1987 | Kissel et al. | 320/150 |
| 4,663,580 | A | 5/1987 | Wortman | 320/153 |
| 4,665,370 | A | 5/1987 | Holland | 324/429 |
| 4,667,143 | A | 5/1987 | Cooper et al. | 320/153 |
| 4,667,279 | A | 5/1987 | Maier | 363/46 |
| 4,678,998 | A | 7/1987 | Muramatsu | 324/427 |
| 4,679,000 | A | 7/1987 | Clark | 324/428 |
| 4,680,528 | A | 7/1987 | Mikami et al. | 320/165 |
| 4,686,442 | A | 8/1987 | Radomski | 320/123 |
| 4,697,134 | A | 9/1987 | Burkum et al. | 320/134 |
| 4,707,795 | A | 11/1987 | Alber et al. | 702/63 |
| 4,709,202 | A | 11/1987 | Koenck et al. | 320/112 |
| 4,710,861 | A | 12/1987 | Kanner | 363/46 |
| 4,719,428 | A | 1/1988 | Liebermann | 324/436 |
| 4,723,656 | A | 2/1988 | Kiernan et al. | 206/705 |
| 4,743,855 | A | 5/1988 | Randin et al. | 324/430 |
| 4,745,349 | A | 5/1988 | Palanisamy et al. | 320/125 |
| 4,773,011 | A | 9/1988 | VanHoose | 701/30 |
| 4,781,629 | A | 11/1988 | Mize | 439/822 |
| D299,909 | S | 2/1989 | Casey | D10/77 |
| 4,816,768 | A | 3/1989 | Champlin | 324/428 |
| 4,820,966 | A | 4/1989 | Fridman | 320/116 |
| 4,825,170 | A | 4/1989 | Champlin | 324/436 |
| 4,847,547 | A | 7/1989 | Eng, Jr. et al. | 320/153 |
| 4,849,700 | A | 7/1989 | Morioka et al. | 324/427 |
| 4,874,679 | A | 10/1989 | Miyagawa | 429/91 |
| 4,876,495 | A | 10/1989 | Palanisamy et al. | 320/106 |
| 4,881,038 | A | 11/1989 | Champlin | 324/428 |
| 4,885,523 | A | 12/1989 | Koenck | 230/131 |
| 4,888,716 | A | 12/1989 | Ueno | 702/63 |
| 4,901,007 | A | 2/1990 | Sworm | 324/110 |
| 4,907,176 | A | 3/1990 | Bahnick et al. | 364/551.01 |
| 4,912,416 | A | 3/1990 | Champlin | 324/430 |
| 4,913,116 | A | 4/1990 | Katogi et al. | 123/406.32 |
| 4,926,330 | A | 5/1990 | Abe et al. | 701/33 |
| 4,929,931 | A | 5/1990 | McCuen | 340/636.15 |
| 4,931,738 | A | 6/1990 | MacIntyre et al. | 324/435 |
| 4,932,905 | A | 6/1990 | Richards | 439/822 |
| 4,933,845 | A | 6/1990 | Hayes | 710/104 |
| 4,934,957 | A | 6/1990 | Bellusci | 439/504 |
| 4,937,528 | A | 6/1990 | Palanisamy | 324/430 |
| 4,947,124 | A | 8/1990 | Hauser | 324/430 |
| 4,949,046 | A | 8/1990 | Seyfang | 324/427 |
| 4,956,597 | A | 9/1990 | Heavey et al. | 320/129 |
| 4,965,738 | A | 10/1990 | Bauer et al. | 320/136 |
| 4,968,941 | A | 11/1990 | Rogers | 324/428 |
| 4,968,942 | A | 11/1990 | Palanisamy | 324/430 |
| 4,969,834 | A | 11/1990 | Johnson | 439/141 |
| 4,983,086 | A | 1/1991 | Hatrock | 411/259 |
| 5,004,979 | A | 4/1991 | Marino et al. | 324/160 |

(56) References Cited

U.S. PATENT DOCUMENTS

| | | | |
|---|---|---|---|
| 5,030,916 A | 7/1991 | Bokitch | 324/503 |
| 5,032,825 A | 7/1991 | Kuznicki | 340/636.15 |
| 5,034,893 A | 7/1991 | Fisher | 701/99 |
| 5,037,778 A | 8/1991 | Stark et al. | 228/121 |
| 5,047,722 A | 9/1991 | Wurst et al. | 324/430 |
| 5,081,565 A | 1/1992 | Nabha et al. | 362/465 |
| 5,087,881 A | 2/1992 | Peacock | 324/378 |
| 5,095,223 A | 3/1992 | Thomas | 307/110 |
| 5,108,320 A | 4/1992 | Kimber | 439/883 |
| 5,109,213 A | 4/1992 | Williams | 340/447 |
| 5,126,675 A | 6/1992 | Yang | 324/435 |
| 5,130,658 A | 7/1992 | Bohmer | 324/435 |
| 5,140,269 A | 8/1992 | Champlin | 324/433 |
| 5,144,218 A | 9/1992 | Bosscha | 320/139 |
| 5,144,248 A | 9/1992 | Alexandres et al. | 324/428 |
| D330,338 S | 10/1992 | Wang | D10/77 |
| 5,159,272 A | 10/1992 | Rao et al. | 324/429 |
| 5,160,881 A | 11/1992 | Schramm et al. | 322/7 |
| 5,164,653 A | 11/1992 | Reem | |
| 5,168,208 A | 12/1992 | Schultz et al. | 322/25 |
| 5,170,124 A | 12/1992 | Blair et al. | 324/434 |
| 5,179,335 A | 1/1993 | Nor | 320/159 |
| 5,187,382 A | 2/1993 | Kondo | |
| 5,194,799 A | 3/1993 | Tomantschger | 320/103 |
| 5,204,611 A | 4/1993 | Nor et al. | 320/145 |
| 5,214,370 A | 5/1993 | Harm et al. | 320/152 |
| 5,214,385 A | 5/1993 | Gabriel et al. | 324/434 |
| 5,223,747 A | 6/1993 | Tschulena | 257/713 |
| 5,241,275 A | 8/1993 | Fang | 324/430 |
| 5,254,952 A | 10/1993 | Salley et al. | 324/429 |
| 5,266,880 A | 11/1993 | Newland | 320/125 |
| 5,278,759 A | 1/1994 | Berra et al. | 701/1 |
| 5,281,919 A | 1/1994 | Palanisamy | 324/427 |
| 5,281,920 A | 1/1994 | Wurst | 324/430 |
| 5,295,078 A | 3/1994 | Stich et al. | 700/297 |
| 5,298,797 A | 3/1994 | Redl | 327/387 |
| 5,300,874 A | 4/1994 | Shimamoto et al. | 320/106 |
| 5,302,902 A | 4/1994 | Groehl | 324/434 |
| 5,313,152 A | 5/1994 | Wozniak et al. | 320/118 |
| 5,315,287 A | 5/1994 | Sol | 340/455 |
| 5,321,626 A | 6/1994 | Palladino | 702/63 |
| 5,321,627 A | 6/1994 | Reher | 702/63 |
| 5,323,337 A | 6/1994 | Wilson et al. | 702/73 |
| 5,325,041 A | 6/1994 | Briggs | 320/149 |
| 5,331,268 A | 7/1994 | Patino et al. | 320/116 |
| 5,332,927 A | 7/1994 | Paul et al. | 307/66 |
| 5,336,993 A | 8/1994 | Thomas et al. | 324/158.1 |
| 5,338,515 A | 8/1994 | Dalla Betta et al. | 422/95 |
| 5,339,018 A | 8/1994 | Brokaw | 320/147 |
| 5,343,380 A | 8/1994 | Champlin | 363/46 |
| 5,345,384 A | 9/1994 | Przybyla et al. | 701/29.1 |
| 5,347,163 A | 9/1994 | Yoshimura | 307/66 |
| 5,352,968 A | 10/1994 | Reni et al. | 320/136 |
| 5,357,519 A | 10/1994 | Martin et al. | 371/15.1 |
| 5,365,160 A | 11/1994 | Leppo et al. | 320/160 |
| 5,365,453 A | 11/1994 | Startup et al. | 702/36 |
| 5,369,364 A | 11/1994 | Renirie et al. | 324/430 |
| 5,381,096 A | 1/1995 | Hirzel | 324/427 |
| 5,384,540 A * | 1/1995 | Dessel | 324/539 |
| 5,387,871 A | 2/1995 | Tsai | 324/429 |
| 5,394,093 A * | 2/1995 | Cervas | 324/556 |
| 5,402,007 A | 3/1995 | Center et al. | 290/40 B |
| 5,410,754 A | 4/1995 | Klotzbach et al. | 370/466 |
| 5,412,308 A | 5/1995 | Brown | 323/267 |
| 5,412,323 A | 5/1995 | Kato et al. | 324/429 |
| 5,425,041 A | 6/1995 | Seko et al. | 372/45.01 |
| 5,426,371 A | 6/1995 | Salley et al. | 324/429 |
| 5,426,416 A | 6/1995 | Jefferies et al. | 340/664 |
| 5,430,645 A | 7/1995 | Keller | 364/424.01 |
| 5,432,025 A | 7/1995 | Cox | 29/65 |
| 5,432,426 A | 7/1995 | Yoshida | 320/160 |
| 5,434,495 A | 7/1995 | Toko | 320/135 |
| 5,435,185 A | 7/1995 | Eagan | 73/587 |
| 5,442,274 A | 8/1995 | Tamai | 320/146 |
| 5,445,026 A | 8/1995 | Eagan | 73/591 |
| 5,449,996 A | 9/1995 | Matsumoto et al. | 320/148 |
| 5,449,997 A | 9/1995 | Gilmore et al. | 320/148 |
| 5,451,881 A | 9/1995 | Finger | 324/433 |
| 5,453,027 A | 9/1995 | Buell et al. | 439/433 |
| 5,457,377 A | 10/1995 | Jonsson | 324/430 |
| 5,459,660 A | 10/1995 | Berra | 701/33 |
| 5,469,043 A | 11/1995 | Cherng et al. | 320/161 |
| 5,485,090 A | 1/1996 | Stephens | 324/433 |
| 5,488,300 A | 1/1996 | Jamieson | 324/432 |
| 5,504,674 A | 4/1996 | Chen et al. | 705/4 |
| 5,508,599 A | 4/1996 | Koenck | 320/138 |
| 5,519,383 A | 5/1996 | De La Rosa | 340/636.15 |
| 5,528,148 A | 6/1996 | Rogers | 320/137 |
| 5,537,967 A | 7/1996 | Tashiro et al. | 123/192.1 |
| 5,541,489 A | 7/1996 | Dunstan | 320/134 |
| 5,546,317 A | 8/1996 | Andrieu | 702/63 |
| 5,548,273 A | 8/1996 | Nicol et al. | 340/439 |
| 5,550,485 A | 8/1996 | Falk | 324/772 |
| 5,561,380 A | 10/1996 | Sway-Tin et al. | 324/509 |
| 5,562,501 A | 10/1996 | Kinoshita et al. | 439/852 |
| 5,563,496 A | 10/1996 | McClure | 320/128 |
| 5,572,136 A | 11/1996 | Champlin | 324/426 |
| 5,573,611 A | 11/1996 | Koch et al. | 152/152.1 |
| 5,574,355 A | 11/1996 | McShane et al. | 320/161 |
| 5,578,915 A | 11/1996 | Crouch, Jr. et al. | 324/428 |
| 5,583,416 A | 12/1996 | Klang | 320/160 |
| 5,585,416 A | 12/1996 | Audett et al. | 522/35 |
| 5,585,728 A | 12/1996 | Champlin | 324/427 |
| 5,589,757 A | 12/1996 | Klang | 320/160 |
| 5,592,093 A | 1/1997 | Klingbiel | 324/426 |
| 5,592,094 A | 1/1997 | Ichikawa | 324/427 |
| 5,596,260 A | 1/1997 | Moravec et al. | 320/135 |
| 5,596,261 A | 1/1997 | Suyama | 320/152 |
| 5,598,098 A | 1/1997 | Champlin | 324/430 |
| 5,602,462 A | 2/1997 | Stich et al. | 323/258 |
| 5,606,242 A | 2/1997 | Hull et al. | 320/106 |
| 5,614,788 A | 3/1997 | Mullins et al. | 315/82 |
| 5,621,298 A | 4/1997 | Harvey | 320/134 |
| 5,631,536 A | 5/1997 | Tseng | 320/15 |
| 5,631,831 A | 5/1997 | Bird et al. | 701/34.4 |
| 5,633,985 A | 5/1997 | Severson et al. | 704/267 |
| 5,637,978 A | 6/1997 | Kellett et al. | 320/104 |
| 5,642,031 A | 6/1997 | Brotto | 320/156 |
| 5,644,212 A | 7/1997 | Takahashi | |
| 5,650,937 A | 7/1997 | Bounaga | 702/65 |
| 5,652,501 A | 7/1997 | McClure et al. | 340/636.15 |
| 5,653,659 A | 8/1997 | Kunibe et al. | 477/111 |
| 5,654,623 A | 8/1997 | Shiga et al. | 320/106 |
| 5,656,920 A | 8/1997 | Cherng et al. | 324/431 |
| 5,661,368 A | 8/1997 | Deol et al. | 315/82 |
| 5,666,040 A | 9/1997 | Bourbeau | 320/118 |
| 5,675,234 A | 10/1997 | Greene | 340/636.11 |
| 5,677,077 A | 10/1997 | Faulk | 429/90 |
| 5,684,678 A | 11/1997 | Barrett | 363/17 |
| 5,691,621 A | 11/1997 | Phuoc et al. | 320/134 |
| 5,699,050 A | 12/1997 | Kanazawa | 340/636.13 |
| 5,701,089 A | 12/1997 | Perkins | 4/772 |
| 5,705,929 A | 1/1998 | Caravello et al. | 324/430 |
| 5,707,015 A | 1/1998 | Guthrie | 241/120 |
| 5,710,503 A | 1/1998 | Sideris et al. | 320/116 |
| 5,711,648 A | 1/1998 | Hammerslag | 414/800 |
| 5,712,795 A | 1/1998 | Layman et al. | 700/297 |
| 5,717,336 A | 2/1998 | Basell et al. | 324/430 |
| 5,717,937 A | 2/1998 | Fritz | 713/300 |
| 5,721,688 A | 2/1998 | Bramwell | 324/426 |
| 5,732,074 A | 3/1998 | Spaur et al. | 370/313 |
| 5,739,667 A | 4/1998 | Matsuda et al. | 320/128 |
| 5,744,962 A | 4/1998 | Alber et al. | 324/426 |
| 5,745,044 A | 4/1998 | Hyatt, Jr. et al. | 340/5.23 |
| 5,747,189 A | 5/1998 | Perkins | 429/91 |
| 5,747,909 A | 5/1998 | Syverson et al. | 310/156.56 |
| 5,747,967 A | 5/1998 | Muljadi et al. | 320/148 |
| 5,754,417 A | 5/1998 | Nicollini | 363/60 |
| 5,757,192 A | 5/1998 | McShane et al. | 324/427 |
| 5,760,587 A | 6/1998 | Harvey | 324/434 |
| 5,772,468 A | 6/1998 | Kowalski et al. | 439/506 |
| 5,773,962 A | 6/1998 | Nor | 20/134 |
| 5,773,978 A | 6/1998 | Becker | 324/430 |
| 5,778,326 A | 7/1998 | Moroto et al. | 701/22 |

(56) References Cited

U.S. PATENT DOCUMENTS

| | | | |
|---|---|---|---|
| 5,780,974 A | 7/1998 | Pabla et al. | 315/82 |
| 5,780,980 A | 7/1998 | Naito | 318/139 |
| 5,789,899 A | 8/1998 | van Phuoc et al. | 320/112 |
| 5,793,359 A | 8/1998 | Ushikubo | 345/169 |
| 5,796,239 A | 8/1998 | van Phuoc et al. | 320/107 |
| 5,808,469 A | 9/1998 | Kopera | 324/434 |
| 5,811,979 A | 9/1998 | Rhein | 324/718 |
| 5,818,201 A | 10/1998 | Stockstad et al. | 320/119 |
| 5,818,234 A | 10/1998 | McKinnon | 324/433 |
| 5,820,407 A | 10/1998 | Morse et al. | 439/504 |
| 5,821,756 A | 10/1998 | McShane et al. | 324/430 |
| 5,821,757 A | 10/1998 | Alvarez et al. | 324/434 |
| 5,825,174 A | 10/1998 | Parker | 324/106 |
| 5,831,435 A | 11/1998 | Troy | 324/426 |
| 5,832,396 A | 11/1998 | Moroto et al. | 701/22 |
| 5,850,113 A | 12/1998 | Weimer et al. | 307/125 |
| 5,862,515 A | 1/1999 | Kobayashi et al. | 702/63 |
| 5,865,638 A | 2/1999 | Trafton | 439/288 |
| 5,869,951 A | 2/1999 | Takahashi | 320/104 |
| 5,871,858 A | 2/1999 | Thomsen et al. | 429/7 |
| 5,872,443 A | 2/1999 | Williamson | 320/160 |
| 5,872,453 A | 2/1999 | Shimoyama et al. | 324/433 |
| 5,883,306 A | 3/1999 | Hwang | 73/146.8 |
| 5,884,202 A | 3/1999 | Arjomand | 701/31.4 |
| 5,895,440 A | 4/1999 | Proctor et al. | 702/63 |
| 5,903,154 A | 5/1999 | Zhang et al. | 324/437 |
| 5,903,716 A | 5/1999 | Kimber et al. | 395/114 |
| 5,912,534 A | 6/1999 | Benedict | 315/82 |
| 5,914,605 A | 6/1999 | Bertness | 324/430 |
| 5,916,287 A | 6/1999 | Arjomand et al. | 701/33.2 |
| 5,927,938 A | 7/1999 | Hammerslag | 414/809 |
| 5,929,609 A | 7/1999 | Joy et al. | 322/25 |
| 5,935,180 A | 8/1999 | Fieramosca et al. | 701/29.6 |
| 5,939,855 A | 8/1999 | Proctor et al. | 320/104 |
| 5,939,861 A | 8/1999 | Joko et al. | 320/122 |
| 5,945,829 A | 8/1999 | Bertness | 324/433 |
| 5,946,605 A | 8/1999 | Takahisa et al. | 455/68 |
| 5,950,144 A | 9/1999 | Hall et al. | 702/108 |
| 5,951,229 A | 9/1999 | Hammerslag | 414/398 |
| 5,953,322 A | 9/1999 | Kimball | 370/328 |
| 5,955,951 A | 9/1999 | Wischerop et al. | 340/572.8 |
| 5,961,561 A | 10/1999 | Wakefield, II | 701/29 |
| 5,961,604 A | 10/1999 | Anderson et al. | 709/229 |
| 5,963,012 A | 10/1999 | Garcia et al. | 320/106 |
| 5,969,625 A | 10/1999 | Russo | 340/636.19 |
| 5,973,598 A | 10/1999 | Beigel | 340/572.1 |
| 5,978,805 A | 11/1999 | Carson | 707/10 |
| 5,982,138 A | 11/1999 | Krieger | 320/105 |
| 5,990,664 A | 11/1999 | Rahman | 320/136 |
| 6,002,238 A | 12/1999 | Champlin | 320/134 |
| 6,005,489 A | 12/1999 | Siegle et al. | 340/825.69 |
| 6,005,759 A | 12/1999 | Hart et al. | 361/66 |
| 6,008,652 A | 12/1999 | Theofanopoulos et al. | 324/434 |
| 6,009,369 A | 12/1999 | Boisvert et al. | 701/99 |
| 6,016,047 A | 1/2000 | Notten et al. | 320/137 |
| 6,031,354 A | 2/2000 | Wiley et al. | 320/116 |
| 6,031,368 A | 2/2000 | Klippel et al. | 324/133 |
| 6,037,745 A | 3/2000 | Koike et al. | 320/104 |
| 6,037,749 A | 3/2000 | Parsonage | 320/132 |
| 6,037,751 A | 3/2000 | Klang | 320/160 |
| 6,037,777 A | 3/2000 | Champlin | 324/430 |
| 6,037,778 A | 3/2000 | Makhija | 324/433 |
| 6,046,514 A | 4/2000 | Rouillard et al. | 307/77 |
| 6,051,976 A | 4/2000 | Bertness | 324/426 |
| 6,055,468 A | 4/2000 | Kaman et al. | 701/29 |
| 6,061,638 A | 5/2000 | Joyce | 702/63 |
| 6,064,372 A | 5/2000 | Kahkoska | 345/173 |
| 6,072,299 A | 6/2000 | Kurle et al. | 320/112 |
| 6,072,300 A | 6/2000 | Tsuji | 320/116 |
| 6,075,339 A | 6/2000 | Reipur et al. | 320/110 |
| 6,081,098 A | 6/2000 | Bertness et al. | 320/134 |
| 6,081,109 A | 6/2000 | Seymour et al. | 324/127 |
| 6,081,154 A | 6/2000 | Ezell et al. | 327/540 |
| 6,087,815 A | 7/2000 | Pfeifer et al. | 323/282 |
| 6,091,238 A | 7/2000 | McDermott | 324/207.2 |
| 6,091,245 A | 7/2000 | Bertness | 324/426 |
| 6,094,033 A | 7/2000 | Ding et al. | 320/132 |
| 6,097,193 A | 8/2000 | Bramwell | 324/429 |
| 6,100,670 A | 8/2000 | Levesque | 320/150 |
| 6,100,815 A | 8/2000 | Pailthorp | 324/754.07 |
| 6,104,167 A | 8/2000 | Bertness et al. | 320/132 |
| 6,113,262 A | 9/2000 | Purola et al. | 374/45 |
| 6,114,834 A | 9/2000 | Parise | 320/109 |
| 6,121,880 A | 9/2000 | Scott et al. | 340/572.5 |
| 6,136,914 A | 10/2000 | Hergenrother et al. | 524/495 |
| 6,137,269 A | 10/2000 | Champlin | 20/150 |
| 6,140,797 A | 10/2000 | Dunn | 320/105 |
| 6,141,608 A | 10/2000 | Rother | 701/29.6 |
| 6,144,185 A | 11/2000 | Dougherty et al. | 320/132 |
| 6,147,598 A | 11/2000 | Murphy et al. | 340/426.19 |
| 6,150,793 A | 11/2000 | Lesesky et al. | 320/104 |
| 6,158,000 A | 12/2000 | Collins | 713/1 |
| 6,161,640 A | 12/2000 | Yamaguchi | 180/65.8 |
| 6,163,156 A | 12/2000 | Bertness | 324/426 |
| 6,164,063 A | 12/2000 | Mendler | 60/274 |
| 6,167,349 A | 12/2000 | Alvarez | 702/63 |
| 6,172,483 B1 | 1/2001 | Champlin | 320/134 |
| 6,172,505 B1 | 1/2001 | Bertness | 324/430 |
| 6,177,737 B1 | 1/2001 | Palfey et al. | 307/64 |
| 6,181,545 B1 | 1/2001 | Amatucci et al. | 361/502 |
| 6,184,656 B1 | 2/2001 | Karunasiri et al. | 320/119 |
| 6,191,557 B1 | 2/2001 | Gray et al. | 320/132 |
| 6,202,739 B1 | 3/2001 | Pal et al. | 165/104.33 |
| 6,211,651 B1 | 4/2001 | Nemoto | 320/133 |
| 6,211,653 B1 | 4/2001 | Stasko | 320/132 |
| 6,215,275 B1 | 4/2001 | Bean | 320/106 |
| 6,218,805 B1 | 4/2001 | Melcher | 320/105 |
| 6,218,936 B1 | 4/2001 | Imao | 340/447 |
| 6,222,342 B1 | 4/2001 | Eggert et al. | 320/105 |
| 6,222,369 B1 | 4/2001 | Champlin | 324/430 |
| D442,503 S | 5/2001 | Lundbeck et al. | D10/77 |
| 6,225,808 B1 | 5/2001 | Varghese et al. | 324/426 |
| 6,225,898 B1 | 5/2001 | Kamiya et al. | 340/505 |
| 6,236,186 B1 | 5/2001 | Helton et al. | 320/106 |
| 6,236,332 B1 | 5/2001 | Conkright et al. | 340/3.1 |
| 6,236,949 B1 | 5/2001 | Hart | 702/64 |
| 6,238,253 B1 | 5/2001 | Qualls | 439/759 |
| 6,242,887 B1 | 6/2001 | Burke | 320/104 |
| 6,249,124 B1 | 6/2001 | Bertness | 324/426 |
| 6,250,973 B1 | 6/2001 | Lowery et al. | 439/763 |
| 6,254,438 B1 | 7/2001 | Gaunt | 439/755 |
| 6,259,170 B1 | 7/2001 | Limoge et al. | 307/10.8 |
| 6,259,254 B1 | 7/2001 | Klang | 324/427 |
| 6,262,563 B1 | 7/2001 | Champlin | 320/134 |
| 6,262,692 B1 | 7/2001 | Babb | 343/895 |
| 6,263,268 B1 | 7/2001 | Nathanson | 701/29 |
| 6,263,322 B1 | 7/2001 | Kirkevold et al. | 705/400 |
| 6,271,643 B1 | 8/2001 | Becker et al. | 320/112 |
| 6,271,748 B1 | 8/2001 | Derbyshire et al. | 340/442 |
| 6,272,387 B1 * | 8/2001 | Yoon | 700/83 |
| 6,275,008 B1 | 8/2001 | Arai et al. | 320/132 |
| 6,285,191 B1 | 9/2001 | Gollomp et al. | 324/427 |
| 6,294,896 B1 | 9/2001 | Champlin | 320/134 |
| 6,294,897 B1 | 9/2001 | Champlin | 320/153 |
| 6,304,087 B1 | 10/2001 | Bertness | 324/426 |
| 6,307,349 B1 | 10/2001 | Koenck et al. | 320/112 |
| 6,310,481 B2 | 10/2001 | Bertness | 324/430 |
| 6,313,607 B1 | 11/2001 | Champlin | 320/132 |
| 6,313,608 B1 | 11/2001 | Varghese et al. | 320/132 |
| 6,316,914 B1 | 11/2001 | Bertness | 320/134 |
| 6,320,351 B1 | 11/2001 | Ng et al. | 320/104 |
| 6,323,650 B1 | 11/2001 | Bertness et al. | 324/426 |
| 6,324,042 B1 | 11/2001 | Andrews | 361/93.2 |
| 6,329,793 B1 | 12/2001 | Bertness et al. | 320/132 |
| 6,331,762 B1 * | 12/2001 | Bertness | 320/134 |
| 6,332,113 B1 | 12/2001 | Bertness | 702/63 |
| 6,346,795 B2 | 2/2002 | Haraguchi et al. | 320/136 |
| 6,347,958 B1 | 2/2002 | Tsai | 439/488 |
| 6,351,102 B1 | 2/2002 | Troy | 320/139 |
| 6,356,042 B1 | 3/2002 | Kahlon et al. | 318/138 |
| 6,356,083 B1 | 3/2002 | Ying | 324/426 |
| 6,359,441 B1 | 3/2002 | Bertness | 324/426 |
| 6,359,442 B1 | 3/2002 | Henningson et al. | 324/426 |
| 6,363,303 B1 | 3/2002 | Bertness | 701/29 |

(56) References Cited

U.S. PATENT DOCUMENTS

| | | | |
|---|---|---|---|
| RE37,677 E | 4/2002 | Irie | 315/83 |
| 6,377,031 B1 | 4/2002 | Karuppana et al. | 323/220 |
| 6,384,608 B1 | 5/2002 | Namaky | 324/430 |
| 6,388,448 B1 | 5/2002 | Cervas | 324/426 |
| 6,389,337 B1 | 5/2002 | Kolls | 701/31.6 |
| 6,392,414 B2 | 5/2002 | Bertness | 324/429 |
| 6,396,278 B1 | 5/2002 | Makhija | 324/402 |
| 6,407,554 B1 | 6/2002 | Godau et al. | 324/503 |
| 6,411,098 B1 | 6/2002 | Laletin | 324/436 |
| 6,417,669 B1 | 7/2002 | Champlin | 324/426 |
| 6,420,852 B1 | 7/2002 | Sato | 320/134 |
| 6,424,157 B1 | 7/2002 | Gollomp et al. | 324/430 |
| 6,424,158 B2 | 7/2002 | Klang | 324/433 |
| 6,433,512 B1 | 8/2002 | Birkler et al. | 320/132 |
| 6,437,957 B1 | 8/2002 | Karuppana et al. | 361/78 |
| 6,441,585 B1 | 8/2002 | Bertness | 320/132 |
| 6,445,158 B1 | 9/2002 | Bertness et al. | 320/104 |
| 6,448,778 B1 * | 9/2002 | Rankin | 324/503 |
| 6,449,726 B1 | 9/2002 | Smith | 713/340 |
| 6,456,036 B1 | 9/2002 | Thandiwe | 320/106 |
| 6,456,045 B1 | 9/2002 | Troy et al. | 320/139 |
| 6,465,908 B1 | 10/2002 | Karuppana et al. | 307/31 |
| 6,466,025 B1 | 10/2002 | Klang | 324/429 |
| 6,466,026 B1 | 10/2002 | Champlin | 324/430 |
| 6,469,511 B1 | 10/2002 | Vonderhaar et al. | 324/425 |
| 6,473,659 B1 | 10/2002 | Shah et al. | 700/79 |
| 6,477,478 B1 | 11/2002 | Jones et al. | 702/102 |
| 6,495,990 B2 | 12/2002 | Champlin | 320/132 |
| 6,497,209 B1 | 12/2002 | Karuppana et al. | 123/179.3 |
| 6,500,025 B1 | 12/2002 | Moenkhaus et al. | 439/502 |
| 6,505,507 B1 | 1/2003 | Imao | 73/146.5 |
| 6,507,196 B2 | 1/2003 | Thomsen et al. | 324/436 |
| 6,526,361 B1 | 2/2003 | Jones et al. | 702/63 |
| 6,529,723 B1 | 3/2003 | Bentley | 455/405 |
| 6,531,848 B1 | 3/2003 | Chitsazan et al. | 320/153 |
| 6,532,425 B1 | 3/2003 | Boost et al. | 702/63 |
| 6,533,316 B2 | 3/2003 | Breed et al. | 280/735 |
| 6,534,992 B2 | 3/2003 | Meissner et al. | 324/426 |
| 6,534,993 B2 | 3/2003 | Bertness | 324/433 |
| 6,536,536 B1 | 3/2003 | Gass et al. | 173/2 |
| 6,544,078 B2 | 4/2003 | Palmisano et al. | 439/762 |
| 6,545,599 B2 | 4/2003 | Derbyshire et al. | 340/442 |
| 6,556,019 B2 | 4/2003 | Bertness | 324/426 |
| 6,566,883 B1 | 5/2003 | Vonderhaar et al. | 324/426 |
| 6,570,385 B1 | 5/2003 | Roberts et al. | 324/426 |
| 6,577,107 B2 | 6/2003 | Kechmire | 320/139 |
| 6,586,941 B2 | 7/2003 | Bertness et al. | 324/426 |
| 6,597,150 B1 | 7/2003 | Bertness et al. | 320/104 |
| 6,599,243 B2 | 7/2003 | Woltermann et al. | 600/300 |
| 6,600,815 B1 | 7/2003 | Walding | 379/93.07 |
| 6,611,740 B2 | 8/2003 | Lowrey et al. | 701/29 |
| 6,614,349 B1 | 9/2003 | Proctor et al. | 340/572.1 |
| 6,618,644 B2 | 9/2003 | Bean | 700/231 |
| 6,621,272 B2 | 9/2003 | Champlin | 324/426 |
| 6,623,314 B1 | 9/2003 | Cox et al. | 439/759 |
| 6,624,635 B1 | 9/2003 | Lui | 24/426 |
| 6,628,011 B2 | 9/2003 | Droppo et al. | 307/43 |
| 6,629,054 B2 | 9/2003 | Makhija et al. | 702/113 |
| 6,633,165 B2 | 10/2003 | Bertness | 324/426 |
| 6,635,974 B1 | 10/2003 | Karuppana et al. | 307/140 |
| 6,636,790 B1 | 10/2003 | Lightner et al. | 701/31.5 |
| 6,667,624 B1 | 12/2003 | Raichle et al. | 324/522 |
| 6,679,212 B2 | 1/2004 | Kelling | 123/179.28 |
| 6,686,542 B2 | 2/2004 | Zhang | 174/74 |
| 6,696,819 B2 | 2/2004 | Bertness | 320/134 |
| 6,707,303 B2 | 3/2004 | Bertness et al. | 324/426 |
| 6,732,031 B1 | 5/2004 | Lightner et al. | 701/31.4 |
| 6,736,941 B2 | 5/2004 | Oku et al. | 203/68 |
| 6,737,831 B2 | 5/2004 | Champlin | 320/132 |
| 6,738,697 B2 | 5/2004 | Breed | 701/29 |
| 6,740,990 B2 | 5/2004 | Tozuka et al. | 307/9.1 |
| 6,744,149 B1 | 6/2004 | Karuppana et al. | 307/31 |
| 6,745,153 B2 | 6/2004 | White et al. | 702/184 |
| 6,759,849 B2 | 7/2004 | Bertness | 324/426 |
| 6,771,073 B2 | 8/2004 | Henningson et al. | 324/426 |
| 6,777,945 B2 | 8/2004 | Roberts et al. | 324/426 |
| 6,781,344 B1 | 8/2004 | Hedegor et al. | 320/106 |
| 6,781,382 B2 | 8/2004 | Johnson | 324/426 |
| 6,784,635 B2 | 8/2004 | Larson | 320/104 |
| 6,784,637 B2 | 8/2004 | Raichle et al. | 320/107 |
| 6,788,025 B2 | 9/2004 | Bertness et al. | 320/104 |
| 6,795,782 B2 | 9/2004 | Bertness et al. | 702/63 |
| 6,796,841 B1 | 9/2004 | Cheng et al. | 439/620.3 |
| 6,805,090 B2 | 10/2004 | Bertness et al. | 123/198 |
| 6,806,716 B2 | 10/2004 | Bertness et al. | 324/426 |
| 6,825,669 B2 | 11/2004 | Raichle et al. | 324/426 |
| 6,832,141 B2 | 12/2004 | Skeen et al. | 701/31.4 |
| 6,842,707 B2 | 1/2005 | Raichle et al. | 702/62 |
| 6,845,279 B1 | 1/2005 | Gilmore et al. | 700/115 |
| 6,850,037 B2 | 2/2005 | Bertness | 320/132 |
| 6,856,162 B1 | 2/2005 | Greatorex et al. | 324/764.01 |
| 6,856,972 B1 | 2/2005 | Yun et al. | 705/36 R |
| 6,871,151 B2 | 3/2005 | Bertness | 702/63 |
| 6,885,195 B2 | 4/2005 | Bertness | 324/426 |
| 6,888,468 B2 | 5/2005 | Bertness | 340/636.15 |
| 6,891,378 B2 | 5/2005 | Bertness et al. | 324/426 |
| 6,904,796 B2 | 6/2005 | Pacsai et al. | 73/146.8 |
| 6,906,522 B2 | 6/2005 | Bertness et al. | 324/426 |
| 6,906,523 B2 | 6/2005 | Bertness et al. | 324/426 |
| 6,906,624 B2 | 6/2005 | McClelland et al. | 340/442 |
| 6,909,287 B2 | 6/2005 | Bertness | 324/427 |
| 6,909,356 B2 | 6/2005 | Brown et al. | 340/3.2 |
| 6,911,825 B2 | 6/2005 | Namaky | 324/426 |
| 6,913,483 B2 | 7/2005 | Restaino et al. | 439/504 |
| 6,914,413 B2 | 7/2005 | Bertness et al. | 320/104 |
| 6,919,725 B2 | 7/2005 | Bertness et al. | 324/433 |
| 6,930,485 B2 | 8/2005 | Bertness et al. | 324/426 |
| 6,933,727 B2 | 8/2005 | Bertness et al. | 324/426 |
| 6,941,234 B2 | 9/2005 | Bertness et al. | 702/63 |
| 6,957,133 B1 | 10/2005 | Hunt et al. | 701/32.4 |
| 6,967,484 B2 | 11/2005 | Bertness | 324/426 |
| 6,972,662 B1 | 12/2005 | Ohkawa et al. | 340/10.1 |
| 6,983,212 B2 | 1/2006 | Burns | 702/63 |
| 6,993,421 B2 | 1/2006 | Pillar et al. | 701/29.4 |
| 6,998,847 B2 | 2/2006 | Bertness et al. | 324/426 |
| 7,003,410 B2 | 2/2006 | Bertness et al. | 702/63 |
| 7,003,411 B2 | 2/2006 | Bertness | 702/63 |
| 7,012,433 B2 | 3/2006 | Smith et al. | 324/426 |
| 7,015,674 B2 | 3/2006 | VonderHaar | 320/103 |
| 7,029,338 B1 | 4/2006 | Orange et al. | 439/755 |
| 7,034,541 B2 | 4/2006 | Bertness et al. | 324/426 |
| 7,039,533 B2 | 5/2006 | Bertness et al. | 702/63 |
| 7,042,346 B2 | 5/2006 | Paulsen | 340/438 |
| 7,058,525 B2 | 6/2006 | Bertness et al. | 702/63 |
| 7,069,979 B2 | 7/2006 | Tobias | 165/104.33 |
| 7,081,755 B2 | 7/2006 | Klang et al. | 324/426 |
| 7,089,127 B2 | 8/2006 | Thibedeau et al. | 702/63 |
| 7,098,666 B2 | 8/2006 | Patino | 324/433 |
| 7,102,556 B2 | 9/2006 | White | 341/141 |
| 7,106,070 B2 | 9/2006 | Bertness et al. | 324/538 |
| 7,116,109 B2 | 10/2006 | Klang | 324/426 |
| 7,119,686 B2 | 10/2006 | Bertness et al. | 340/572.1 |
| 7,120,488 B2 | 10/2006 | Nova et al. | 600/2 |
| 7,126,341 B2 | 10/2006 | Bertness et al. | 324/426 |
| 7,129,706 B2 | 10/2006 | Kalley | 324/426 |
| 7,154,276 B2 | 12/2006 | Bertness | 324/503 |
| 7,170,393 B2 | 1/2007 | Martin | 340/10.1 |
| 7,177,925 B2 | 2/2007 | Carcido et al. | 709/223 |
| 7,182,147 B2 | 2/2007 | Cutler et al. | 173/1 |
| 7,184,905 B2 | 2/2007 | Stefan | 702/63 |
| 7,198,510 B2 | 4/2007 | Bertness | 439/500 |
| 7,200,424 B2 | 4/2007 | Tischer et al. | 455/567 |
| 7,202,636 B2 | 4/2007 | Reynolds et al. | 320/166 |
| 7,208,914 B2 | 4/2007 | Klang | 320/132 |
| 7,209,850 B2 | 4/2007 | Brott et al. | 324/426 |
| 7,209,860 B2 | 4/2007 | Trsar et al. | 702/183 |
| 7,212,887 B2 | 5/2007 | Shah et al | 700/276 |
| 7,219,023 B2 | 5/2007 | Banke et al. | 702/58 |
| 7,233,128 B2 | 6/2007 | Brost et al. | 320/132 |
| 7,235,977 B2 | 6/2007 | Koran et al. | 324/426 |
| 7,246,015 B2 | 7/2007 | Bertness et al. | 702/63 |
| 7,272,519 B2 | 9/2007 | Lesesky et al. | 702/63 |
| 7,287,001 B1 | 10/2007 | Falls et al. | 705/22 |
| 7,295,936 B2 | 11/2007 | Bertness et al. | 702/63 |

(56) References Cited

U.S. PATENT DOCUMENTS

| | | | |
|---|---|---|---|
| 7,319,304 B2 | 1/2008 | Veloo et al. | 320/134 |
| 7,339,477 B2 | 3/2008 | Puzio et al. | 340/572.1 |
| 7,363,175 B2 | 4/2008 | Bertness et al. | 702/63 |
| 7,398,176 B2 | 7/2008 | Bertness | 702/140 |
| 7,408,358 B2 | 8/2008 | Knopf | 324/426 |
| 7,425,833 B2 | 9/2008 | Bertness et al. | 324/426 |
| 7,446,536 B2 | 11/2008 | Bertness | 324/426 |
| 7,453,238 B2 | 11/2008 | Melichar | 320/132 |
| 7,479,763 B2 | 1/2009 | Bertness | 320/134 |
| 7,498,767 B2 | 3/2009 | Brown et al. | 320/107 |
| 7,501,795 B2 | 3/2009 | Bertness et al. | 320/134 |
| 7,505,856 B2 | 3/2009 | Restaino et al. | 702/63 |
| 7,545,146 B2 | 6/2009 | Klang et al. | 324/426 |
| 7,557,586 B1 | 7/2009 | Vonderhaar et al. | 324/437 |
| 7,590,476 B2 | 9/2009 | Shumate | 701/31.6 |
| 7,592,776 B2 | 9/2009 | Tsukamoto et al. | 320/136 |
| 7,595,643 B2 | 9/2009 | Klang | 324/426 |
| 7,598,699 B2 | 10/2009 | Restaino et al. | 320/105 |
| 7,598,743 B2 | 10/2009 | Bertness | 324/426 |
| 7,598,744 B2 | 10/2009 | Bertness et al. | 324/426 |
| 7,619,417 B2 | 11/2009 | Klang | 324/427 |
| 7,642,786 B2 | 1/2010 | Philbrook | 324/426 |
| 7,642,787 B2 | 1/2010 | Bertness et al. | 324/426 |
| 7,656,162 B2 | 2/2010 | Vonderhaar et al. | 324/426 |
| 7,657,386 B2 | 2/2010 | Thibedeau et al. | 702/63 |
| 7,667,437 B2 | 2/2010 | Johnson et al. | 320/150 |
| 7,679,325 B2 | 3/2010 | Seo | 20/116 |
| 7,684,908 B1 | 3/2010 | Ogilvie et al. | 701/29.6 |
| 7,688,074 B2 | 3/2010 | Cox et al. | 324/426 |
| 7,698,179 B2 | 4/2010 | Leung et al. | 705/28 |
| 7,705,602 B2 | 4/2010 | Bertness | 324/426 |
| 7,706,991 B2 | 4/2010 | Bertness et al. | 702/63 |
| 7,710,119 B2 | 5/2010 | Bertness | 324/426 |
| 7,723,993 B2 | 5/2010 | Klang | 324/431 |
| 7,728,556 B2 | 6/2010 | Yano et al. | 320/134 |
| 7,728,597 B2 | 6/2010 | Bertness | 324/426 |
| 7,744,149 B2 | 6/2010 | Murray et al. | 307/31 |
| 7,751,953 B2 | 7/2010 | Namaky | 701/33.2 |
| 7,772,850 B2 | 8/2010 | Bertness | 324/426 |
| 7,774,151 B2 | 8/2010 | Bertness | 702/63 |
| 7,777,612 B2 | 8/2010 | Sampson et al. | 340/426.1 |
| 7,791,348 B2 | 9/2010 | Brown et al. | 324/426 |
| 7,808,375 B2 | 10/2010 | Bertness et al. | 340/455 |
| 7,848,857 B2 | 12/2010 | Nasr et al. | 701/22 |
| 7,883,002 B2 | 2/2011 | Jin et al. | 235/376 |
| 7,902,990 B2 | 3/2011 | Delmonico et al. | 340/636.1 |
| 7,924,015 B2 | 4/2011 | Bertness | 324/427 |
| 7,940,053 B2 | 5/2011 | Brown et al. | 324/426 |
| 7,990,155 B2 | 8/2011 | Henningson | 324/429 |
| 7,999,505 B2 | 8/2011 | Bertness | 320/104 |
| 8,164,343 B2 | 4/2012 | Bertness | 324/503 |
| 8,306,690 B2 | 11/2012 | Bertness | 701/34.4 |
| 2001/0012738 A1 | 8/2001 | Duperret | 439/835 |
| 2001/0035737 A1 | 11/2001 | Nakanishi et al. | 320/122 |
| 2001/0048215 A1 | 12/2001 | Breed et al. | 280/728.1 |
| 2002/0003423 A1 | 1/2002 | Bertness et al. | 324/426 |
| 2002/0004694 A1 | 1/2002 | McLeod | 701/29 |
| 2002/0007237 A1 | 1/2002 | Phung et al. | 701/33 |
| 2002/0010558 A1 | 1/2002 | Bertness et al. | 702/63 |
| 2002/0021135 A1 | 2/2002 | Li et al. | 324/677 |
| 2002/0027346 A1 | 3/2002 | Breed et al. | 280/735 |
| 2002/0030495 A1 | 3/2002 | Kechmire | 324/427 |
| 2002/0036504 A1 | 3/2002 | Troy et al. | 324/430 |
| 2002/0041175 A1 | 4/2002 | Lauper et al. | 320/106 |
| 2002/0044050 A1 | 4/2002 | Derbyshire et al. | 340/442 |
| 2002/0047711 A1 | 4/2002 | Bertness et al. | 324/426 |
| 2002/0050163 A1 | 5/2002 | Makhija et al. | 73/116 |
| 2002/0074398 A1 | 6/2002 | Lancos et al. | 235/382 |
| 2002/0116140 A1 | 8/2002 | Rider | 702/63 |
| 2002/0118111 A1 | 8/2002 | Brown et al. | 340/573.1 |
| 2002/0121901 A1 | 9/2002 | Hoffman | 324/426 |
| 2002/0128985 A1 | 9/2002 | Greenwald | 705/400 |
| 2002/0130665 A1 | 9/2002 | Bertness et al. | 324/426 |
| 2002/0171428 A1 | 11/2002 | Bertness | 702/63 |
| 2002/0176010 A1 | 11/2002 | Wallach et al. | 348/362 |
| 2003/0006779 A1* | 1/2003 | H. Youval | 324/503 |
| 2003/0009270 A1 | 1/2003 | Breed | 701/29 |
| 2003/0017753 A1 | 1/2003 | Palmisano et al. | 439/762 |
| 2003/0025481 A1 | 2/2003 | Bertness | 324/427 |
| 2003/0036909 A1 | 2/2003 | Kato | 704/275 |
| 2003/0040873 A1 | 2/2003 | Lesesky et al. | 702/57 |
| 2003/0060953 A1 | 3/2003 | Chen | 701/33 |
| 2003/0078743 A1 | 4/2003 | Bertness et al. | 702/63 |
| 2003/0088375 A1 | 5/2003 | Bertness et al. | 702/63 |
| 2003/0124417 A1 | 7/2003 | Bertness et al. | 429/90 |
| 2003/0128011 A1 | 7/2003 | Bertness et al. | |
| 2003/0128036 A1 | 7/2003 | Henningson et al. | 324/426 |
| 2003/0137277 A1 | 7/2003 | Mori et al. | 320/132 |
| 2003/0169018 A1 | 9/2003 | Berels et al. | 320/132 |
| 2003/0169019 A1 | 9/2003 | Oosaki | 320/132 |
| 2003/0171111 A1 | 9/2003 | Clark | 455/414.1 |
| 2003/0177417 A1 | 9/2003 | Malhotra et al. | 714/42 |
| 2003/0184262 A1 | 10/2003 | Makhija | 320/156 |
| 2003/0184306 A1 | 10/2003 | Bertness et al. | 324/426 |
| 2003/0187556 A1 | 10/2003 | Suzuki | 701/29 |
| 2003/0194672 A1 | 10/2003 | Roberts et al. | 431/196 |
| 2003/0197512 A1 | 10/2003 | Miller et al. | 324/426 |
| 2003/0212311 A1 | 11/2003 | Nova et al. | 600/300 |
| 2003/0214395 A1 | 11/2003 | Flowerday et al. | 340/445 |
| 2003/0236656 A1 | 12/2003 | Dougherty | 703/14 |
| 2004/0000590 A1 | 1/2004 | Raichle et al. | 235/462.01 |
| 2004/0000891 A1 | 1/2004 | Raichle et al. | 320/107 |
| 2004/0000893 A1 | 1/2004 | Raichle et al. | 320/135 |
| 2004/0000913 A1 | 1/2004 | Raichle et al. | 324/426 |
| 2004/0000915 A1 | 1/2004 | Raichle et al. | 324/522 |
| 2004/0002824 A1 | 1/2004 | Raichle et al. | 702/63 |
| 2004/0002825 A1 | 1/2004 | Raichle et al. | 702/63 |
| 2004/0002836 A1 | 1/2004 | Raichle et al. | 702/188 |
| 2004/0032264 A1 | 2/2004 | Schoch | 324/426 |
| 2004/0036443 A1 | 2/2004 | Bertness | 320/109 |
| 2004/0044452 A1 | 3/2004 | Bauer et al. | 703/33 |
| 2004/0044454 A1 | 3/2004 | Ross et al. | 701/33 |
| 2004/0049361 A1 | 3/2004 | Hamdan et al. | 702/115 |
| 2004/0051532 A1 | 3/2004 | Smith et al. | 324/426 |
| 2004/0051533 A1 | 3/2004 | Namaky | 324/426 |
| 2004/0051534 A1 | 3/2004 | Kobayashi et al. | 324/429 |
| 2004/0054503 A1 | 3/2004 | Namaky | 702/182 |
| 2004/0064225 A1 | 4/2004 | Jammu et al. | 701/29 |
| 2004/0088087 A1 | 5/2004 | Fukushima et al. | 701/32 |
| 2004/0113588 A1 | 6/2004 | Mikuriya et al. | 320/128 |
| 2004/0145342 A1 | 7/2004 | Lyon | 320/108 |
| 2004/0164706 A1 | 8/2004 | Osborne | 320/116 |
| 2004/0172177 A1 | 9/2004 | Nagai et al. | 701/29 |
| 2004/0178185 A1 | 9/2004 | Yoshikawa et al. | 219/270 |
| 2004/0189309 A1 | 9/2004 | Bertness et al. | 324/426 |
| 2004/0199343 A1 | 10/2004 | Cardinal et al. | 702/63 |
| 2004/0207367 A1 | 10/2004 | Taniguchi et al. | 320/149 |
| 2004/0227523 A1 | 11/2004 | Namaky | 324/537 |
| 2004/0239332 A1 | 12/2004 | Mackel et al. | 324/426 |
| 2004/0251876 A1 | 12/2004 | Bertness et al. | 320/136 |
| 2005/0007068 A1 | 1/2005 | Johnson et al. | 320/110 |
| 2005/0009122 A1 | 1/2005 | Whelan et al. | 435/7.32 |
| 2005/0017726 A1 | 1/2005 | Koran et al. | 324/433 |
| 2005/0017952 A1 | 1/2005 | Hsi | 345/169 |
| 2005/0021294 A1 | 1/2005 | Trsar et al. | 702/183 |
| 2005/0025299 A1 | 2/2005 | Tischer et al. | 379/199 |
| 2005/0043868 A1 | 2/2005 | Mitcham | 701/29 |
| 2005/0057256 A1 | 3/2005 | Bertness | 324/426 |
| 2005/0060070 A1 | 3/2005 | Kapolka et al. | 701/29 |
| 2005/0073314 A1 | 4/2005 | Bertness et al. | 324/433 |
| 2005/0076381 A1 | 4/2005 | Gross | 725/107 |
| 2005/0096809 A1 | 5/2005 | Skeen et al. | 701/29 |
| 2005/0102073 A1 | 5/2005 | Ingram | 701/29 |
| 2005/0128083 A1 | 6/2005 | Puzio et al. | 340/572.1 |
| 2005/0128902 A1 | 6/2005 | Tsai | 369/44.32 |
| 2005/0134282 A1 | 6/2005 | Averbuch | 324/426 |
| 2005/0143882 A1 | 6/2005 | Umezawa | 701/29 |
| 2005/0159847 A1 | 7/2005 | Shah et al. | 700/276 |
| 2005/0162172 A1 | 7/2005 | Bertness | 324/426 |
| 2005/0168226 A1 | 8/2005 | Quint et al. | 324/426 |
| 2005/0173142 A1 | 8/2005 | Cutler et al. | 173/181 |
| 2005/0182536 A1 | 8/2005 | Doyle et al. | 701/29 |
| 2005/0212521 A1 | 9/2005 | Bertness et al. | 324/426 |
| 2005/0213874 A1 | 9/2005 | Kline | 385/15 |

(56) References Cited

U.S. PATENT DOCUMENTS

| | | | |
|---|---|---|---|
| 2005/0218902 A1 | 10/2005 | Restaino et al. | 324/433 |
| 2005/0231205 A1 | 10/2005 | Bertness et al. | 324/426 |
| 2005/0254106 A9 | 11/2005 | Silverbrook et al. | 358/539 |
| 2005/0256617 A1 | 11/2005 | Cawthorne et al. | 701/22 |
| 2005/0258241 A1 | 11/2005 | McNutt et al. | 235/385 |
| 2006/0012330 A1 | 1/2006 | Okumura et al. | 320/103 |
| 2006/0017447 A1 | 1/2006 | Bertness | 324/538 |
| 2006/0030980 A1 | 2/2006 | St. Denis | 701/29 |
| 2006/0043976 A1* | 3/2006 | Gervais | 324/508 |
| 2006/0089767 A1 | 4/2006 | Sowa | 701/29 |
| 2006/0095230 A1 | 5/2006 | Grier et al. | 702/183 |
| 2006/0152224 A1 | 7/2006 | Kim et al. | 324/430 |
| 2006/0161313 A1 | 7/2006 | Rogers et al. | 701/1 |
| 2006/0161390 A1 | 7/2006 | Namaky et al. | 702/183 |
| 2006/0217914 A1 | 9/2006 | Bertness | 702/113 |
| 2006/0244457 A1 | 11/2006 | Henningson et al. | 324/426 |
| 2006/0282323 A1 | 12/2006 | Walker et al. | 705/14 |
| 2007/0024460 A1 | 2/2007 | Clark | 340/663 |
| 2007/0026916 A1 | 2/2007 | Juds et al. | 463/1 |
| 2007/0046261 A1 | 3/2007 | Porebski | 320/132 |
| 2007/0088472 A1 | 4/2007 | Ganzhorn et al. | 701/33 |
| 2007/0108942 A1 | 5/2007 | Johnson et al. | 320/132 |
| 2007/0159177 A1 | 7/2007 | Bertness et al. | 324/426 |
| 2007/0182576 A1 | 8/2007 | Proska et al. | 340/636.1 |
| 2007/0194791 A1 | 8/2007 | Huang | 324/430 |
| 2007/0194793 A1 | 8/2007 | Bertness | 324/503 |
| 2007/0205983 A1 | 9/2007 | Naimo | 345/160 |
| 2007/0259256 A1 | 11/2007 | Le Canut et al. | 429/90 |
| 2008/0036421 A1 | 2/2008 | Seo et al. | 320/132 |
| 2008/0059014 A1 | 3/2008 | Nasr et al. | 701/22 |
| 2008/0086246 A1 | 4/2008 | Bolt et al. | 701/29 |
| 2008/0094068 A1 | 4/2008 | Scott | 324/426 |
| 2008/0169818 A1 | 7/2008 | Lesesky et al. | 324/426 |
| 2008/0303528 A1 | 12/2008 | Kim | 324/430 |
| 2008/0303529 A1 | 12/2008 | Nakamura et al. | 324/433 |
| 2008/0315830 A1 | 12/2008 | Bertness | 320/104 |
| 2009/0006476 A1 | 1/2009 | Andreasen et al. | 707/104.1 |
| 2009/0024266 A1 | 1/2009 | Bertness | 701/22 |
| 2009/0085571 A1 | 4/2009 | Bertness | 324/426 |
| 2009/0146800 A1 | 6/2009 | Grimlund et al. | 340/505 |
| 2009/0198372 A1 | 8/2009 | Hammerslag | 700/226 |
| 2009/0247020 A1 | 10/2009 | Gathman et al. | 439/759 |
| 2009/0276115 A1 | 11/2009 | Chen | 701/32 |
| 2010/0023198 A1 | 1/2010 | Hamilton | 701/29 |
| 2010/0145780 A1 | 6/2010 | Nishikawa et al. | 705/14.11 |
| 2010/0314950 A1 | 12/2010 | Rutkowski et al. | 307/125 |
| 2011/0004427 A1 | 1/2011 | Gorbold et al. | 702/63 |
| 2011/0215767 A1 | 9/2011 | Johnson et al. | 320/136 |
| 2011/0273181 A1 | 11/2011 | Park et al. | 324/429 |
| 2012/0046824 A1 | 2/2012 | Ruther et al. | 701/31.5 |
| 2012/0074904 A1 | 3/2012 | Rutkowski et al. | 320/112 |
| 2012/0256494 A1 | 10/2012 | Kesler | 307/104 |
| 2013/0158782 A1 | 6/2013 | Bertness et al. | 701/34.4 |
| 2013/0311124 A1 | 11/2013 | Van Bremen | 702/104 |
| 2014/0002094 A1 | 1/2014 | Champlin | 324/426 |

FOREIGN PATENT DOCUMENTS

| | | |
|---|---|---|
| DE | 29 26 716 B1 | 1/1981 |
| DE | 196 38 324 | 9/1996 |
| DE | 10 2008 036 595 A1 | 2/2010 |
| EP | 0 022 450 A1 | 1/1981 |
| EP | 0 391 694 A2 | 4/1990 |
| EP | 0 476 405 A2 | 9/1991 |
| EP | 0 637 754 A1 | 2/1995 |
| EP | 0 772 056 A1 | 5/1997 |
| EP | 0 982 159 A2 | 3/2000 |
| EP | 1 810 869 A1 | 11/2004 |
| EP | 1 807 710 B1 | 7/2007 |
| EP | 1 807 710 | 1/2010 |
| FR | 2 749 397 | 12/1997 |
| GB | 154 016 | 11/1920 |
| GB | 2 029 586 | 3/1980 |
| GB | 2 088 159 A | 6/1982 |
| GB | 2 246 916 A | 10/1990 |
| GB | 2 275 783 A | 7/1994 |
| GB | 2 387 235 A | 10/2003 |
| JP | 59-17892 | 1/1984 |
| JP | 59-17893 | 1/1984 |
| JP | 59017894 | 1/1984 |
| JP | 59215674 | 12/1984 |
| JP | 60225078 | 11/1985 |
| JP | 62-180284 | 8/1987 |
| JP | 63027776 | 2/1988 |
| JP | 03274479 | 12/1991 |
| JP | 03282276 | 12/1991 |
| JP | 4-8636 | 1/1992 |
| JP | 04095788 | 3/1992 |
| JP | 04131779 | 5/1992 |
| JP | 04372536 | 12/1992 |
| JP | 05211724 A | 8/1993 |
| JP | 5216550 | 8/1993 |
| JP | 7-128414 | 5/1995 |
| JP | 09061505 | 3/1997 |
| JP | 10056744 | 2/1998 |
| JP | 10232273 | 9/1998 |
| JP | 11103503 A | 4/1999 |
| JP | 11-150809 | 6/1999 |
| JP | 11-271409 | 10/1999 |
| JP | 2001057711 A | 2/2001 |
| JP | 2003-346909 | 12/2003 |
| JP | 2006331976 A | 12/2006 |
| JP | 2009-244166 | 10/2009 |
| RU | 2089015 C1 | 8/1997 |
| WO | WO 93/22666 | 11/1993 |
| WO | WO 94/05069 | 3/1994 |
| WO | WO 96/01456 | 1/1996 |
| WO | WO 96/06747 | 3/1996 |
| WO | WO 96/28846 | 9/1996 |
| WO | WO 97/01103 | 1/1997 |
| WO | WO 97/44652 | 11/1997 |
| WO | WO 98/04910 | 2/1998 |
| WO | WO 98/21132 | 5/1998 |
| WO | WO 98/58270 | 12/1998 |
| WO | WO 99/23738 | 5/1999 |
| WO | WO 99/56121 | 11/1999 |
| WO | WO 00/16083 | 3/2000 |
| WO | WO 00/62049 | 10/2000 |
| WO | WO 00/67359 | 11/2000 |
| WO | WO 01/59443 | 2/2001 |
| WO | WO 01/16614 | 3/2001 |
| WO | WO 01/16615 | 3/2001 |
| WO | WO 01/51947 | 7/2001 |
| WO | WO 03/047064 A3 | 6/2003 |
| WO | WO 03/076960 A1 | 9/2003 |
| WO | WO 2004/047215 A1 | 6/2004 |
| WO | WO 2010/007681 | 1/2010 |
| WO | WO 2011/153419 | 12/2011 |

OTHER PUBLICATIONS

Search Report and Written Opinion from PCT Application No. PCT/US2011/038279, dated Sep. 16, 2011. 12 pgs.
"Electrochemical Impedance Spectroscopy in Battery Development and Testing", *Batteries International*, Apr. 1997, pp. 59 and 62-63.
"Battery Impedance", by E. Willihnganz et al., *Electrical Engineering*, Sep. 1959, pp. 922-925.
"Determining the End of Battery Life", by S. DeBardelaben, *IEEE*, 1986, pp. 365-368.
"A Look at the Impedance of a Cell", by S. Debardelaben, *IEEE*, 1988, pp. 394-397.
"The Impedance of Electrical Storage Cells", by N. A. Hampson et al., *Journal of Applied Electrochemistry*, 1980, pp. 3-11.
"A Package for Impedance/Admittance Data Analysis", by B. Boukamp, *Solid State Ionics*, 1986, pp. 136-140.
"Precision of Impedance Spectroscopy Estimates of Bulk, Reaction Rate, and Diffusion Parameters", by J. Macdonald et al., *J. Electroanal. Chem.*, 1991, pp. 1-11.
Internal Resistance: Harbinger of Capacity Loss in Starved Electrolyte Sealed Lead Acid Batteries, by Vaccaro, F. J. et al., *AT&T Bell Laboratories*, 1987 IEEE, Ch. 2477, pp. 128, 131.

(56) References Cited

OTHER PUBLICATIONS

IEEE Recommended Practice for Maintenance, Testings, and Replacement of Large Lead Storage Batteries for Generating Stations and Substations, *The Institute of Electrical and Electronics Engineers, Inc., ANSI/IEEE Std.* 450-1987, Mar. 9, 1987, pp. 7-15.
"Field and Laboratory Studies to Assess the State of Health of Valve-Regulated Lead Acid Batteries: Part I Conductance/Capacity Correlation Studies", by D. Feder et al., *IEEE*, Aug. 1992, pp. 218-233.
"JIS Japanese Industrial Standard-Lead Acid Batteries for Automobiles", *Japanese Standards Association UDC*, 621.355.2:629.113. 006, Nov. 1995.
"Performance of Dry Cells", by C. Hambuechen, Preprint of *Am. Electrochem. Soc.*, Apr. 18-20, 1912, paper No. 19, pp. 1-5.
"A Bridge for Measuring Storage Battery Resistance", by E. Willihncanz, *The Electrochemical Society*, preprint 79-20, Apr. 1941, pp. 253-258.
National Semiconductor Corporation, "High Q Notch Filter", Mar. 1969, Linear Brief 5, Mar. 1969.
Burr-Brown Corporation, "Design a 60 Hz Notch Filter with the UAF42", Jan. 1994, AB-071, 1994.
National Semiconductor Corporation, "LMF90-4$^{th}$-Order Elliptic Notch Filter", Dec. 1994, RRD-B30M115, Dec. 1994.
"Alligator Clips with Wire Penetrators" *J.S. Popper, Inc.* product information, downloaded from http://www.jspopper.com/, prior to Oct. 1, 2002.
"#12 LM78S40 Simple Switcher DC to DC Converter", *ITM e-Catalog*, downloaded from http://www.pcbcafe.com, prior to Oct. 1, 2002.
"Simple DC-DC Converts Allows Use of Single Battery", *Electronix Express*, downloaded from http://www.elexp.com/t_dc-dc.htm, prior to Oct. 1, 2002.
"DC-DC Converter Basics", *Power Designers*, downloaded from http://www.powederdesigners.com/InforWeb.design_center/articles/DC-DC/converter.shtm, prior to Oct. 1, 2002.
"Notification of Transmittal of the International Search Report or the Declaration", PCT/US02/29461, filed Sep. 17, 2002 and mailed Jan. 3, 2003.
"Notification of Transmittal of the International Search Report or the Declaration", PCT/US03/07546, filed Mar. 13, 2003 and mailed Jul. 4, 2001.
"Notification of Transmittal of the International Search Report or the Declaration", PCT/US03/06577, filed Mar. 5, 2003 and mailed Aug. 24, 2003.
"Notification of Transmittal of the International Search Report or the Declaration", PCT/US03/07837, filed Mar. 14, 2003 and mailed Jul. 4, 2003.
"Improved Impedance Spectroscopy Technique for Status Determination of Production Li/SO$_2$ Batteries" Terrill Atwater et al., pp. 10-113, (1992).
"Notification of Transmittal of the International Search Report or the Declaration", PCT/US03/41561; Search Report completed Apr. 13, 2004, mailed May 6, 2004.
"Notification of Transmittal of the International Search Report or the Declaration", PCT/US03/27696, filed Sep. 4, 2003 and mailed Apr. 15, 2004.
"Programming Training Course, 62-000 Series Smart Engine Analyzer", Testproducts Division, Kalamazoo, Michigan, pp. 1-207, (1984).
"Operators Manual, Modular Computer Analyzer Model MCA 3000", Sun Electric Corporation, Crystal Lake, Illinois, pp. 1-1-14-13, (1991).
Supplementary European Search Report Communication for Appl. No. 99917402.2; Sep. 7, 2004.
"Dynamic modelling of lead/acid batteries using impedance spectroscopy for parameter identification", Journal of Power Sources, pp. 69-84, (1997).
Notification of Transmittal of the International Search Report for PCT/US03/30707, filed Sep. 30, 2003 and mailed Nov. 24, 2004.

"A review of impedance measurements for determination of the state-of-charge or state-of-health of secondary batteries", Journal of Power Sources, pp. 59-69, (1998).
"Search Report Under Section 17" for Great Britain Application No. GB0421447.4, date of search Jan. 27, 2005, date of document Jan. 28, 2005.
"Results of Discrete Frequency Immittance Spectroscopy (DFIS) Measurements of Lead Acid Batteries", by K.S. Champlin et al., *Proceedings of 23$^{rd}$ International Teleco Conference (INTELEC)*, published Oct. 2001, IEE, pp. 433-440.
"Examination Report" from the UK Patent Office for App. No. 0417678.0; Jan. 24, 2005.
Wikipedia Online Encyclopedia, INDUCTANCE, 2005, http://en.wikipedia.org/wiki/inductance, pp. 1-5, mutual Inductance, pp. 3,4.
"Professional. BCS System Analyzer Battery-Charger-Starting", pp. 2-8, (2001).
Young Illustrated Encyclopedia Dictionary of Electronics, 1981, Parker Publishing Company, Inc., pp. 318-319.
"DSP Applications in Hybrid Electric Vehicle Powertrain", Miller et al., Proceedings of the American Control Conference, Sand Diego, CA, Jun. 1999; 2 ppg.
"Notification of Transmittal of the International Search Report and the Written Opinion of the International Searching Authority, or the Declaration" for PCT/US2008/008702 filed Jul. 2008; 15 pages.
"A Microprocessor-Based Control System for a Near-Term Electric Vehicle", Bimal K. Bose; IEEE Transactions on Industry Applications, vol. IA-17, No. 6, Nov./Dec. 1981; 0093-9994/81/1100-0626$00.75 © 1981 IEEE, 6 pages.
U.S. Appl. No. 60/387,912, filed Jun. 13, 2002 which is related to U.S. Pat. No. 7,089,127.
"Conductance Testing Compared to Traditional Methods of Evaluating the Capacity of Valve-Regulated Lead-Acid Batteries and Predicting State-of-Health", by D. Feder et al., May 1992, pp. 1-8; (13 total pgs.).
"Field and Laboratory Studies to Assess the State of Health of Valve-Regulated Lead Acid Batteries: Part I—Conductance/Capacity Correlation Studies", by D. Feder at al., Oct. 1992, pp. 1-15; (19 total pgs.).
"Field Application of Conductance Measurements Use to Ascertain Cell/Battery and Inter-Cell Connection State-of-Health in Electric Power Utility Applications", by M. Hlavac et al., Apr. 1993, pp. 1-14; (19 total pgs.).
"Conductance Testing of Standby Batteries in Signaling and Communications Applications for the Purpose of Evaluating Battery State-of-Health", by S. McShane, Apr. 1993, pp. 1-9; (14 total pgs.).
"Condutance Monitoring of Recombination Lead Acid Batteries", by B. Jones, May 1993, pp. 1-6; (11 total pgs.).
"Evaluating the State-of-Health of Lead Acid Flooded and Valve-Regulated Batteries: A Comparison of Conductance Testing vs. Traditional Methods", by M. Hlavac et al., Jun. 1993, pp. 1-15; (20 total pgs.).
"Updated State of Conductance/Capacity Correlation Studies to Determine the State-of-Health of Automotive SLI and Standby Lead Acid Batteries", by D. Feder et al., Sep. 1993, pp. 1-17; (22 total pgs.).
"Field and Laboratory Studies to Access the State-of-Health of Valve-Regulated Lead-Acid Battery Technologies Using Conductance Testing Part II—Further Conductance/Capacity Correlation Studies", by M. Hlavac et al., Sep. 1993, pp. 1-9; (14 total pgs.).
"Field Experience of Testing VRLA Batteries by Measuring Conductance", by M.W. Kniveton, May 1994, pp. 1-4; (9 total pgs.).
"Reducing the Cost of Maintaining VRLA Batteries in Telecom Applications", by M.W. Kniveton, Sep. 1994, pp. 1-5; (10 total pgs.).
"Analysis and Interpretation of Conductance Measurements used to Access the State-of-Health of Valve Regulated Lead Acid Batteries Part III: Analytical Techniques", by M. Hlavac, Nov. 1994, 9 pgs; (13 total pgs.).
"Testing 24 Volt Aircraft Batteries Using Midtronics Conductance Technology", by M. Hlavac et al., Jan. 1995, 9 pgs; (13 total pgs.).
"VRLA Battery Monitoring Using Conductance Technology Part IV: On-Line State-of-Health Monitoring and Thermal Runaway Detection/Prevention", by M. Hlavac et al., Oct. 1995, 9 pgs; (13 total pgs.).

(56) References Cited

OTHER PUBLICATIONS

"VRLA Battery Conductance Monitoring Part V: Strategies for VRLA Battery Testing and Monitoring in Telecom Operating Environments", by M. Hlavac et al., Oct. 1996, 9 pgs; (13 total pgs.).
"Midpoint Conductance Technology Used in Telecommunication Stationary Standby Battery Applications Part VI: Considerations for Deployment of Midpoint Conductance in Telecommunications Power Applications", by M. Troy et al., Oct. 1997, 9 pgs; (13 total pgs.).
"Impedance/Conductance Measurements as an Aid to Determining Replacement Strategies", M. Kniveton, Sep. 1998, pp. 297-301; (9 total pgs.).
"A Fundamentally New Approach to Battery Performance Analysis Using DFRA™/DTIS™ Technology", by K. Champlin et al., Sep. 2000, 8 pgs; (12 total pgs.).
"Battery State of Health Monitoring, Combining Conductance Technology With Other Measurement Parameters for Real-Time Battery Performance Analysis", by D. Cox et la., Mar. 2000, 6 pgs; (10 total pgs.).
Examination Report under section 18(3) for corresponding Great Britain Application No. GB1000773.0, dated Feb. 6, 2012, 2 pages.
Communication from GB1216105.5, dated Sep. 21, 2012.
Notification of Transmittal of the International Search Report and Written Opinion from PCT/US2011/039043, dated Jul. 26, 2012.
Notification of Transmittal of the International Search Report and Written Opinion from PCT/US2011/053886, dated Jul. 27, 2012.
"Field Evaluation of Honda's EV PLUS Battery Packs", by A. Paryani, *IEEE AES Systems Magazine*, Nov. 2000, pp. 21-24.
Office Actions from corresponding U.S. Appl. No. 12/261,336, dated 5/35/11 and Nov. 2, 2010.
Office Actions from corresponding U.S. Appl. No. 11/641,594 dated Mar. 22, 2013; Dec. 10, 2012; Sep. 6, 2011; Oct. 29, 2010; May 24, 2010; Mar. 5, 2010; Sep. 15, 2009; Jun. 1, 2009; Dec. 11, 2008; Aug. 25, 2008; and Feb. 28, 2008.
Office Actions from corresponding U.S. Appl. No. 10/656,526 dated Mar. 10, 2006; Sep. 22, 2005; Apr. 4, 2005; and Oct. 5, 2004.
Search Report from PCT/US2011/047354, dated Nov. 11, 2011.
Written Opinion from PCT/US2011/047354, dated Nov. 11, 2011.
First Office Action (Notification of Reasons for Rejections) dated Dec. 3, 2013 in related Japanese patent application No. 2013-513370, 9 pgs. Including English Translation.
Official Action dated Jan. 22, 2014 in Korean patent application No. 10-2012-7033020, 2 pgs including English Translation.
Official Action dated Feb. 20, 2014 in Korean patent application No. 10-2013-7004814, 6 pgs including English Translation.
First Office Action for Chinese Patent Application No. 201180011597.4, dated May 6, 2014, 20 pages.
Office Action from Korean Application No. 10/2012-7033020, dated Jul. 29, 2014.
Office Action for Chinese Patent Application No. 201180038844.X, dated Jul. 1, 2014.
Office Action for Chinese Patent Application No. 201180030045.8, dated Jul. 21, 2014.
Office Action for German Patent Application No. 1120111030643 dated Aug. 28, 2014.
Office Action from Japanese Patent Application No. 2013-513370, dated Aug. 5, 2014.
Office Action from Japanese Patent Application No. 2013-531839, dated Jul. 8, 2014.
Office Action for German Patent Application No. 103 32 625.1, dated Nov. 7, 2014, 14 pages.
Office Action from Chinese Patent Application No. 201180038844.X, dated Dec. 8, 2014.
Office Action from CN Application No. 201180011597.4, dated Jan. 6, 2015.
Office Action for Chinese Patent Application no. 201180030045.8, dated Mar. 24, 2015.
Office Action for Japanese Patent Application No. 2013-531839, dated Mar. 31, 2015.
Notification of Transmittal of the International Search Report and Written Opinion from PCT/US2014/069661, dated Mar. 26, 2015.
Office Action for Chinese Patent Application No. 201180038844.X, dated Jun. 8, 2015.
Office Action from Chinese Patent Application No. 201180011597.4 dated Jun. 3, 2015.
European Search Report from European Application No. EP 15151426.2, dated Jun. 1, 2015.

\* cited by examiner

METHOD AND APPARATUS FOR MEASURING A PARAMETER OF A VEHICLE ELECTRICAL SYSTEM

The present application is based on and claims the benefit of U.S. provisional patent application Ser. No. 61/330,497, filed May 3, 2010, the present application is also a Continuation-In-Part of and claims priority of U.S. patent application Ser. No. 12/261,336, filed Oct. 30, 2008, which is a Continuation-In-Part of U.S. patent application Ser. No. 11/641,594, filed Dec. 19, 2006, which is a Divisional of U.S. patent application Ser. No. 10/656,526, filed Sep. 5, 2003, now U.S. Pat. No. 7,154,276, the contents of which are hereby incorporated by reference in their entirety.

BACKGROUND OF THE INVENTION

The present invention relates to the measurement of electrical parameters of a vehicle electrical system. More specifically, the present invention relates to measuring an electrical parameter of an electrical system of a vehicle using a plurality of connections to the electrical system.

U.S. Pat. No. 3,873,911, issued Mar. 25, 1975, to Champlin; U.S. Pat. No. 3,909,708, issued Sep. 30, 1975, to Champlin; U.S. Pat. No. 4,816,768, issued Mar. 28, 1989, to Champlin; U.S. Pat. No. 4,825,170, issued Apr. 25, 1989, to Champlin; U.S. Pat. No. 4,881,038, issued Nov. 14, 1989, to Champlin; U.S. Pat. No. 4,912,416, issued Mar. 27, 1990, to Champlin; U.S. Pat. No. 5,140,269, issued Aug. 18, 1992, to Champlin; U.S. Pat. No. 5,343,380, issued Aug. 30, 1994; U.S. Pat. No. 5,572,136, issued Nov. 5, 1996; U.S. Pat. No. 5,574,355, issued Nov. 12, 1996; U.S. Pat. No. 5,583,416, issued Dec. 10, 1996; U.S. Pat. No. 5,585,728, issued Dec. 17, 1996; U.S. Pat. No. 5,589,757, issued Dec. 31, 1996; U.S. Pat. No. 5,592,093, issued Jan. 7, 1997; U.S. Pat. No. 5,598,098, issued Jan. 28, 1997; U.S. Pat. No. 5,656,920, issued Aug. 12, 1997; U.S. Pat. No. 5,757,192, issued May 26, 1998; U.S. Pat. No. 5,821,756, issued Oct. 13, 1998; U.S. Pat. No. 5,831,435, issued Nov. 3, 1998; U.S. Pat. No. 5,871,858, issued Feb. 16, 1999; U.S. Pat. No. 5,914,605, issued Jun. 22, 1999; U.S. Pat. No. 5,945,829, issued Aug. 31, 1999; U.S. Pat. No. 6,002,238, issued Dec. 14, 1999; U.S. Pat. No. 6,037,751, issued Mar. 14, 2000; U.S. Pat. No. 6,037,777, issued Mar. 14, 2000; U.S. Pat. No. 6,051,976, issued Apr. 18, 2000; U.S. Pat. No. 6,081,098, issued Jun. 27, 2000; U.S. Pat. No. 6,091,245, issued Jul. 18, 2000; U.S. Pat. No. 6,104,167, issued Aug. 15, 2000; U.S. Pat. No. 6,137,269, issued Oct. 24, 2000; U.S. Pat. No. 6,163,156, issued Dec. 19, 2000; U.S. Pat. No. 6,172,483, issued Jan. 9, 2001; U.S. Pat. No. 6,172,505, issued Jan. 9, 2001; U.S. Pat. No. 6,222,369, issued Apr. 24, 2001; U.S. Pat. No. 6,225,808, issued May 1, 2001; U.S. Pat. No. 6,249,124, issued Jun. 19, 2001; U.S. Pat. No. 6,259,254, issued Jul. 10, 2001; U.S. Pat. No. 6,262,563, issued Jul. 17, 2001; U.S. Pat. No. 6,294,896, issued Sep. 25, 2001; U.S. Pat. No. 6,294,897, issued Sep. 25, 2001; U.S. Pat. No. 6,304,087, issued Oct. 16, 2001; U.S. Pat. No. 6,310,481, issued Oct. 30, 2001; U.S. Pat. No. 6,313,607, issued Nov. 6, 2001; U.S. Pat. No. 6,313,608, issued Nov. 6, 2001; U.S. Pat. No. 6,316,914, issued Nov. 13, 2001; U.S. Pat. No. 6,323,650, issued Nov. 27, 2001; U.S. Pat. No. 6,329,793, issued Dec. 11, 2001; U.S. Pat. No. 6,331,762, issued Dec. 18, 2001; U.S. Pat. No. 6,332,113, issued Dec. 18, 2001; U.S. Pat. No. 6,351,102, issued Feb. 26, 2002; U.S. Pat. No. 6,359,441, issued Mar. 19, 2002; U.S. Pat. No. 6,363,303, issued Mar. 26, 2002; U.S. Pat. No. 6,377,031, issued Apr. 23, 2002; U.S. Pat. No. 6,392,414, issued May 21, 2002; U.S. Pat. No. 6,417,669, issued Jul. 9, 2002; U.S. Pat. No. 6,424,158, issued Jul. 23, 2002; U.S. Pat. No. 6,441,585, issued Aug. 17, 2002; U.S. Pat. No. 6,437,957, issued Aug. 20, 2002; U.S. Pat. No. 6,445,158, issued Sep. 3, 2002; U.S. Pat. No. 6,456,045; U.S. Pat. No. 6,466,025, issued Oct. 15, 2002; U.S. Pat. No. 6,465,908, issued Oct. 15, 2002; U.S. Pat. No. 6,466,026, issued Oct. 15, 2002; U.S. Pat. No. 6,469,511, issued Nov. 22, 2002; U.S. Pat. No. 6,495,990, issued Dec. 17, 2002; U.S. Pat. No. 6,497,209, issued Dec. 24, 2002; U.S. Pat. No. 6,507,196, issued Jan. 14, 2003; U.S. Pat. No. 6,534,993; issued Mar. 18, 2003; U.S. Pat. No. 6,544,078, issued Apr. 8, 2003; U.S. Pat. No. 6,556,019, issued Apr. 29, 2003; U.S. Pat. No. 6,566,883, issued May 20, 2003; U.S. Pat. No. 6,586,941, issued Jul. 1, 2003; U.S. Pat. No. 6,597,150, issued Jul. 22, 2003; U.S. Pat. No. 6,621,272, issued Sep. 16, 2003; U.S. Pat. No. 6,623,314, issued Sep. 23, 2003; U.S. Pat. No. 6,633,165, issued Oct. 14, 2003; U.S. Pat. No. 6,635,974, issued Oct. 21, 2003; U.S. Pat. No. 6,707,303, issued Mar. 16, 2004; U.S. Pat. No. 6,737,831, issued May 18, 2004; U.S. Pat. No. 6,744,149, issued Jun. 1, 2004; U.S. Pat. No. 6,759,849, issued Jul. 6, 2004; U.S. Pat. No. 6,781,382, issued Aug. 24, 2004; U.S. Pat. No. 6,788,025, filed Sep. 7, 2004; U.S. Pat. No. 6,795,782, issued Sep. 21, 2004; U.S. Pat. No. 6,805,090, filed Oct. 19, 2004; U.S. Pat. No. 6,806,716, filed Oct. 19, 2004; U.S. Pat. No. 6,850,037, filed Feb. 1, 2005; U.S. Pat. No. 6,850,037, issued Feb. 1, 2005; U.S. Pat. No. 6,871,151, issued Mar. 22, 2005; U.S. Pat. No. 6,885,195, issued Apr. 26, 2005; U.S. Pat. No. 6,888,468, issued May 3, 2005; U.S. Pat. No. 6,891,378, issued May 10, 2005; U.S. Pat. No. 6,906,522, issued Jun. 14, 2005; U.S. Pat. No. 6,906,523, issued Jun. 14, 2005; U.S. Pat. No. 6,909,287, issued Jun. 21, 2005; U.S. Pat. No. 6,914,413, issued Jul. 5, 2005; U.S. Pat. No. 6,913,483, issued Jul. 5, 2005; U.S. Pat. No. 6,930,485, issued Aug. 16, 2005; U.S. Pat. No. 6,933,727, issued Aug. 23, 200; U.S. Pat. No. 6,941,234, filed Sep. 6, 2005; U.S. Pat. No. 6,967,484, issued Nov. 22, 2005; U.S. Pat. No. 6,998,847, issued Feb. 14, 2006; U.S. Pat. No. 7,003,410, issued Feb. 21, 2006; U.S. Pat. No. 7,003,411, issued Feb. 21, 2006; U.S. Pat. No. 7,012,433, issued Mar. 14, 2006; U.S. Pat. No. 7,015,674, issued Mar. 21, 2006; U.S. Pat. No. 7,034,541, issued Apr. 25, 2006; U.S. Pat. No. 7,039,533, issued May 2, 2006; U.S. Pat. No. 7,058,525, issued Jun. 6, 2006; U.S. Pat. No. 7,081,755, issued Jul. 25, 2006; U.S. Pat. No. 7,106,070, issued Sep. 12, 2006; U.S. Pat. No. 7,116,109, issued Oct. 3, 2006; U.S. Pat. No. 7,119,686, issued Oct. 10, 2006; and U.S. Pat. No. 7,126,341, issued Oct. 24, 2006; U.S. Pat. No. 7,154,276, issued Dec. 26, 2006; U.S. Pat. No. 7,198,510, issued Apr. 3, 2007; U.S. Pat. No. 7,363,175, issued Apr. 22, 2008; U.S. Pat. No. 7,208,914, issued Apr. 24, 2007; U.S. Pat. No. 7,246,015, issued Jul. 17, 2007; U.S. Pat. No. 7,295,936, issued Nov. 13, 2007; U.S. Pat. No. 7,319,304, issued Jan. 15, 2008; U.S. Pat. No. 7,363,175, issued Apr. 22, 2008; U.S. Pat. No. 7,398,176, issued Jul. 8, 2008; U.S. Pat. No. 7,408,358, issued Aug. 5, 2008; U.S. Pat. No. 7,425,833, issued Sep. 16, 2008; U.S. Pat. No. 7,446,536, issued Nov. 4, 2008; U.S. Pat. No. 7,479,763, issued Jan. 20, 2009; U.S. Pat. No. 7,498,767, issued Mar. 3, 2009; U.S. Pat. No. 7,501,795, issued Mar. 10, 2009; U.S. Pat. No. 7,505,856, issued Mar. 17, 2009; U.S. Pat. No. 7,545,146, issued Jun. 9, 2009; U.S. Pat. No. 7,557,586, issued Jul. 7, 2009; U.S. Pat. No. 7,595,643, issued Sep. 29, 2009; U.S. Pat. No. 7,598,699, issued Oct. 6, 2009; U.S. Pat. No. 7,598,744, issued Oct. 6, 2009; U.S. Pat. No. 7,598,743, issued Oct. 6, 2009; U.S. Pat. No. 7,619,417, issued Nov. 17, 2009; U.S. Pat. No. 7,642,786, issued Jan. 5, 2010; U.S. Pat. No. 7,642,787, issued Jan. 5, 2010; U.S. Pat. No. 7,656,162, issued Feb. 2, 2010; U.S. Pat. No. 7,688,074, issued Mar. 30, 2010; U.S. Pat. No. 7,705,602, issued Apr. 27, 2010; U.S. Pat. No. 7,706,992, issued Apr. 27, 2010; U.S. Pat. No. 7,710,119, issued May 4, 2010; U.S. Pat. No. 7,723,993, issued May 25, 2010; U.S. Pat. No. 7,728,597, issued Jun. 1, 2010; U.S. Pat. No. 7,772,850, issued Aug. 10, 2010; U.S. Pat. No. 7,774,151, issued Aug. 10, 2010; U.S. Pat. No. 7,777,612, issued Aug. 17, 2010; U.S. Pat. No. 7,791,348, issued Sep. 7, 2010; U.S. Pat. No. 7,808,375, issued Oct. 5, 2010; U.S. Pat. No. 7,924,015, issued Apr. 12, 2011; U.S. patent application Ser. No. 09/780,146, filed Feb. 9, 2001, entitled STORAGE BATTERY WITH INTEGRAL BATTERY TESTER; U.S. patent application Ser. No. 09/756,638, filed Jan. 8, 2001, entitled METHOD AND APPARATUS FOR DETERMINING BATTERY PROPERTIES FROM COMPLEX IMPEDANCE/ADMITTANCE; U.S. patent application Ser. No. 09/862,783, filed May 21, 2001, entitled METHOD AND APPARATUS FOR TESTING CELLS AND BATTERIES EMBEDDED IN SERIES/PARALLEL SYSTEMS; U.S. patent application Ser. No. 09/880,473, filed Jun. 13, 2001; entitled BATTERY TEST MODULE; U.S. patent application Ser. No. 10/042,451, filed Jan. 8, 2002, entitled BATTERY CHARGE CONTROL DEVICE; U.S. patent application Ser. No. 10/109,734, filed Mar. 28, 2002, entitled APPARATUS AND METHOD FOR COUNTERACTING SELF DISCHARGE IN A STORAGE BATTERY; U.S. patent application Ser. No. 10/112,998, filed Mar. 29, 2002, entitled BATTERY TESTER WITH BATTERY REPLACEMENT OUTPUT; U.S. patent application Ser. No. 10/263,473, filed Oct. 2, 2002, entitled ELECTRONIC BATTERY TESTER WITH RELATIVE TEST OUTPUT; U.S. patent application Ser. No. 10/310,385, filed Dec. 5, 2002, entitled BATTERY TEST MODULE; U.S. patent application Ser. No. 09/653,963, filed Sep. 1, 2000, entitled SYSTEM AND METHOD FOR CONTROLLING POWER GENERATION AND STORAGE; U.S. patent application Ser. No. 10/174,110, filed Jun. 18, 2002, entitled DAYTIME RUNNING LIGHT CONTROL USING AN INTELLIGENT POWER MANAGEMENT SYSTEM; U.S. patent application Ser. No. 10/258,441, filed Apr. 9, 2003, entitled CURRENT MEASURING CIRCUIT SUITED FOR BATTERIES; U.S. patent application Ser. No. 10/681,666, filed Oct. 8, 2003, entitled ELECTRONIC BATTERY TESTER WITH PROBE LIGHT; U.S. patent application Ser. No. 10/791,141, filed Mar. 2, 2004, entitled METHOD AND APPARATUS FOR AUDITING A BATTERY TEST; U.S. patent application Ser. No. 10/867,385, filed Jun. 14, 2004, entitled ENERGY MANAGEMENT SYSTEM FOR AUTOMOTIVE VEHICLE; U.S. patent application Ser. No. 10/958,812, filed Oct. 5, 2004, entitled SCAN TOOL FOR ELECTRONIC BATTERY TESTER; U.S. Ser. No. 60/587,232, filed Dec. 14, 2004, entitled CELLTRON ULTRA, U.S. Ser. No. 60/653,537, filed Feb. 16, 2005, entitled CUSTOMER MANAGED WARRANTY CODE; U.S. Ser. No. 60/665,070, filed Mar. 24, 2005, entitled OHMMETER PROTECTION CIRCUIT; U.S. Ser. No. 60,694,199, filed Jun. 27, 2005, entitled GEL BATTERY CONDUCTANCE COMPENSATION; U.S. Ser. No. 60/705,389, filed Aug. 4, 2005, entitled PORTABLE TOOL THEFT PREVENTION SYSTEM, U.S. patent application Ser. No. 11/207,419, filed Aug. 19, 2005, entitled SYSTEM FOR AUTOMATICALLY GATHERING BATTERY INFORMATION FOR USE DURING BATTERY TESTER/CHARGING, U.S. Ser. No. 60/712,322, filed Aug. 29, 2005, entitled AUTOMOTIVE VEHICLE ELECTRICAL SYSTEM DIAGNOSTIC DEVICE, U.S. Ser. No. 60/713,168, filed Aug. 31, 2005, entitled LOAD TESTER SIMULATION WITH DISCHARGE COMPENSATION, U.S. Ser. No. 60/731,881, filed Oct. 31, 2005, entitled PLUG-IN FEATURES FOR BATTERY TESTERS; U.S. Ser. No. 60/731,887, filed Oct. 31, 2005, entitled AUTOMOTIVE VEHICLE ELECTRICAL SYSTEM DIAGNOSTIC DEVICE; U.S. patent application Ser. No. 11/304,004, filed Dec. 14, 2005, entitled BATTERY TESTER THAT CALCULATES ITS OWN REFERENCE VALUES; U.S. Ser. No. 60/751,853, filed Dec. 20, 2005, entitled BATTERY MONITORING SYSTEM; U.S. patent application Ser. No. 11/304,004, filed Dec. 14, 2005, entitled BATTERY TESTER WITH CALCULATES ITS OWN REFERENCE VALUES; U.S. Ser. No. 60/751,853, filed Dec. 20, 2005, entitled BATTERY MONITORING SYSTEM; U.S. patent application Ser. No. 11/356,443, filed Feb. 16, 2006, entitled ELECTRONIC BATTERY TESTER WITH NETWORK COMMUNICATION; U.S. patent application Ser. No. 11/519,481, filed Sep. 12, 2006, entitled BROAD-BAND LOW-CONDUCTANCE CABLES FOR MAKING KELVIN CONNECTIONS TO ELECTROCHEMICAL CELLS AND BATTERIES; U.S. Ser. No. 60/847,064, filed Sep. 25, 2006, entitled STATIONARY BATTERY MONITORING ALGORITHMS; U.S. patent application Ser. No. 11/641,594, filed Dec. 19, 2006, entitled METHOD AND APPARATUS FOR MEASURING A PARAMETER OF A VEHICLE ELECTRONIC SYSTEM; U.S. Ser. No. 60/950,182, filed Jul. 17, 2007, entitled BATTERY TESTER FOR HYBRID VEHICLE; U.S. Ser. No. 60/973,879, filed Sep. 20, 2007, entitled ELECTRONIC BATTERY TESTER FOR TESTING STATIONARY BATTERIES; U.S. patent application Ser. No. 11/931,907, filed Oct. 31, 2007, entitled BATTERY MAINTENANCE WITH PROBE LIGHT; U.S. Ser. No. 60/992,798, filed Dec. 6, 2007, entitled STORAGE BATTERY AND BATTERY TESTER; U.S. Ser. No. 61/061,848, filed Jun. 16, 2008, entitled KELVIN CLAMP FOR ELECTRONICALLY COUPLING TO A BATTERY CONTACT; U.S. patent application Ser. No. 12/168,264, filed Jul. 7, 2008, entitled BATTERY TESTERS WITH SECONDARY FUNCTIONALITY; U.S. patent application Ser. No. 12/174,894, filed Jul. 17, 2008, entitled BATTERY TESTER FOR ELECTRIC VEHICLE; U.S. patent application Ser. No. 12/204,141, filed Sep. 4, 2008, entitled ELECTRONIC BATTERY TESTER OR CHARGER WITH DATABUS CONNECTION; U.S. patent application Ser. No. 12/328,022, filed Dec. 4, 2008, entitled STORAGE BATTERY AND BATTERY TESTER; U.S. patent application Ser. No. 12/416,457, filed Apr. 1, 2009, entitled SYSTEM FOR AUTOMATICALLY GATHERING BATTERY INFORMATION; U.S. patent application Ser. No. 12/416,453, filed Apr. 1, 2009, entitled INTEGRATED TAG READER AND ENVIRONMENT SENSOR; U.S. patent application Ser. No. 12/416,445, filed Apr. 1, 2009, entitled SIMPLIFICATION OF INVENTORY MANAGEMENT; U.S. patent application Ser. No. 12/485,459, filed Jun. 16, 2009, entitled CLAMP FOR ELECTRONICALLY COUPLING TO A BATTERY CONTACT; U.S. patent application Ser. No. 12/498,642, filed Jul. 7, 2009, entitled ELECTRONIC BATTERY TESTER; U.S. patent application Ser. No. 12/697,485, filed Feb. 1, 2010, entitled ELECTRONIC BATTERY TESTER; U.S. patent application Ser. No. 12/698,375, filed Feb. 2, 2010, entitled ELECTRONIC BATTERY TESTER; U.S. patent application Ser. No. 12/712,456, filed Feb. 25, 2010, entitled METHOD AND APPARATUS FOR DETECTING CELL DETERIORATION IN AN ELECTROCHEMICAL CELL OR BATTERY; U.S. Ser. No. 61/311,485, filed Mar. 8, 2010, entitled BATTERY TESTER WITH DATABUS FOR COMMUNICATING WITH VEHICLE ELECTRICAL SYSTEM; U.S. Ser. No. 61/313,893, filed Mar. 15, 2010, entitled USE OF BATTERY MANUFACTURE/SELL DATE IN DIAGNOSIS AND RECOVERY OF DISCHARGED BATTERIES; U.S. patent application Ser. No. 12/758,407, filed Apr. 12, 2010, entitled ELECTRONIC BATTERY TESTER WITH NETWORK COMMUNICATION; U.S. patent application Ser. No. 12/765,323, filed Apr. 22, 2010, entitled AUTOMOTIVE VEHICLE ELECTRICAL SYSTEM DIAGNOSTIC DEVICE; U.S. patent application Ser. No. 12/769,911, filed Apr. 29, 2010, entitled STATIONARY BATTERY TESTER; U.S. Ser. No. 61/330,497, filed May 3, 2010, entitled MAGIC WAND WITH ADVANCED HARNESS DETECTION; U.S. patent application Ser. No. 12/786,890, filed May 25, 2010, entitled BATTERY TESTER WITH PROMOTION FEATURE; U.S. Ser. No. 61/348,901, filed May 27, 2010, entitled ELECTRONIC BATTERY TESTER; U.S. patent application Ser. No. 29/362,827, filed Jun. 1, 2010, entitled ELECTRONIC BATTERY TESTER; U.S. Ser. No. 61/351,017, filed Jun. 3, 2010, entitled IMPROVED ELECTRIC VEHICLE AND HYBRID ELECTRIC VEHICLE BATTERY MODULE BALANCER; U.S. patent application Ser. No. 12/818,290, filed Jun. 18, 2010, entitled BATTERY MAINTENANCE DEVICE WITH THERMAL BUFFER; U.S. Ser. No. 61/373,045, filed Aug. 12, 2010, entitled ELECTRONIC BATTERY TESTER FOR TESTING STATIONERY STORAGE BATTERY; U.S. patent application Ser. No. 12/888,689, filed Sep. 23, 2010, entitled BATTERY TESTER FOR ELECTRIC VEHICLE; U.S. patent application Ser. No. 12/894,951, filed Sep. 30, 2010, entitled BATTERY PACK MAINTENANCE FOR ELECTRIC VEHICLES; U.S. Ser. No. 61/411,162, filed Nov. 8, 2010, entitled ELECTRONIC BATTERY TESTER; U.S. patent application Ser. No. 13/037,641, filed Mar. 1, 2011, entitled MONITOR FOR FRONT TERMINAL BATTERIES; U.S. patent application Ser. No. 13/048,365, filed Mar. 15, 2011, entitled ELECTRONIC BATTERY TESTER WITH BATTERY AGE UNIT; which are incorporated herein by reference in their entirety.

There is an ongoing need to measure parameters of electrical systems of vehicles and heavy equipment. Such measurements can be used to diagnose operation, failure or impending failure of components or subsystems of electrical systems. For example, in electrical systems used in vehicles, measurement of electrical parameters of such systems can be used to diagnose operation of the system or indicate that maintenance is required before ultimate failure.

One particular measurement is the resistance of cabling used in the vehicle. For example, one such cable or set of cables connects the battery the of vehicle to the starter motor. The starter motor has a relatively large current draw and even a relatively small cable resistance can have a significant impact on operation of the starter motor.

Because the cable resistance is relatively small it typically cannot be measured using a standard ohm meter or other techniques which are normally used to measure resistance. One technique which has been used to measure the cable resistance is to run a very large current through the cable and measure the voltage drop. However, this is cumbersome and requires components capable of handling the large current.

SUMMARY OF THE INVENTION

A vehicle electrical system tester for testing the electrical system of a vehicle is provided. The electrical system has a wiring harness which extends between components of the vehicle and includes a plurality of wires. The vehicle electrical system tester is configured to measure an electrical parameter of at least one of the plurality of wires through a first connection to coupled to a first end of the at least one of the plurality of wires and a second connection coupled to a second end of the at least one of the plurality of wires. An electrical signal is applied between the first and second ends of the at least one of the plurality of wires and the electrical parameter of the at least one of the plurality of wires is responsively measured.

DETAILED DESCRIPTION OF THE PREFERRED EMBODIMENTS

Figure 1:
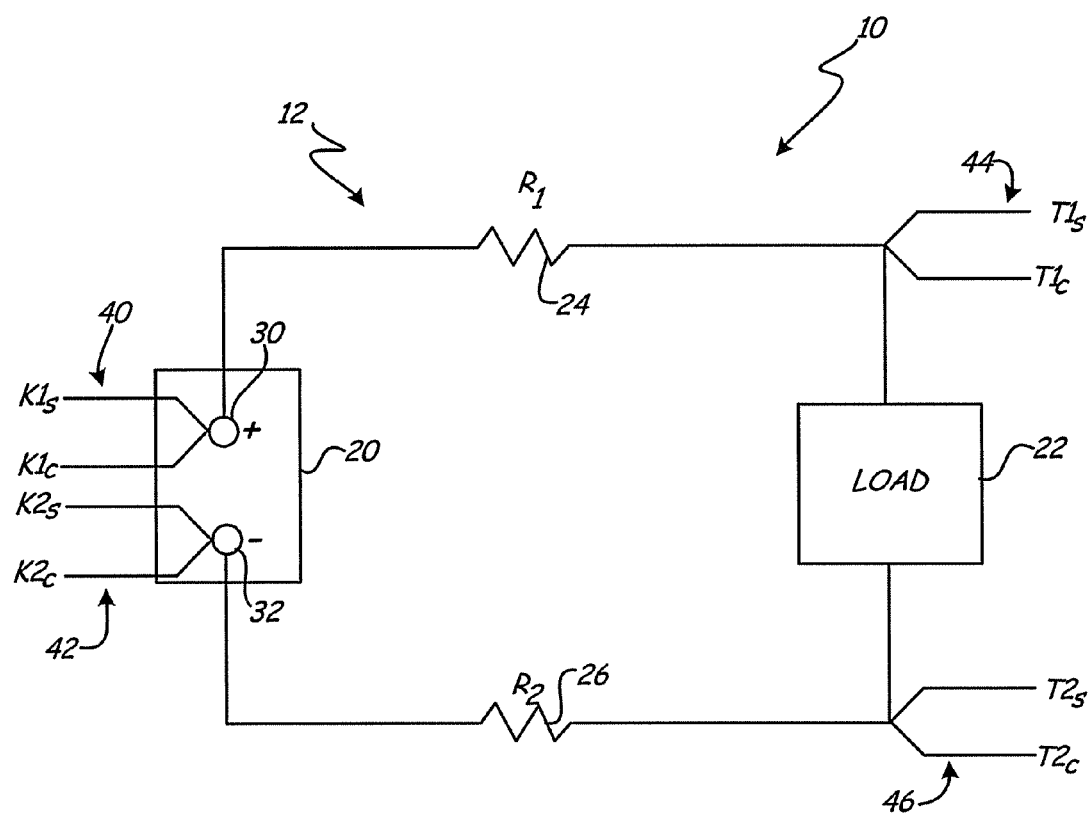
FIG. 1 is a simplified diagram of an electrical system of a vehicle.

FIG. 1 is a simplified diagram of an electrical system 10 of a vehicle 12. Electrical system 10 includes a battery 20, a load 22 and cables 24 and 26 which connect load 22 to the positive terminal 30 of battery 20 and the negative terminal 32 of battery 20, respectively. Cables 24 and 26 are illustrated as having resistances $R_1$ and $R_2$, respectively.

FIG. 1 also shows Kelvin connections 40 and 42 coupled to the positive terminal 30 and the negative terminal 32 of battery 20 respectively. Kelvin connection 40 has a sense connection $K1_S$ and a current connection $K1_C$. Similarly, Kelvin connection 42 has a sense connection $K2_S$ and a current connection $K2_C$. FIG. 1 also illustrates test connections 44 and 46. In the embodiment of FIG. 1, these are illustrated as being Kelvin connections, however the present invention is not limited to this arrangement. Test connection 44 is connected between load 22 and cable 24. Similarly, test connection 46 is connected between load 22 and cable 26. Test connection 44 includes a sense connection $T1_S$ and a current connection $T1_C$. Test connection 46 includes a sense connection $T2_S$ and a current connection $T2_C$.

As discussed in the Background section, the resistances $R_1$ and $R_2$ of cables 24 or 26 can impact the amount of power which can be delivered to load 22. Even if the resistance values are relatively small, if a relatively large current passes through cables 24 and 26, the resultant voltage drop can significantly reduce the voltage across load 22 and therefore the amount of power which can be delivered to load 22. In many instances, it is desirable to measure the resistance $R_1$ and $R_2$ of cables 24 and 26, respectively, in order to identify a cable with a resistance which is too high. One technique which has been used to measure the resistance of the cables is to pass a large current through the cable and measure the resulting voltage drop across the cable. However, this is a cumbersome test and requires electrical test equipment which is capable of handling the large current draw. The present invention provides an apparatus and technique for measuring the resistance of a cable in a configuration similar to that shown in FIG. 1.

Figure 2:
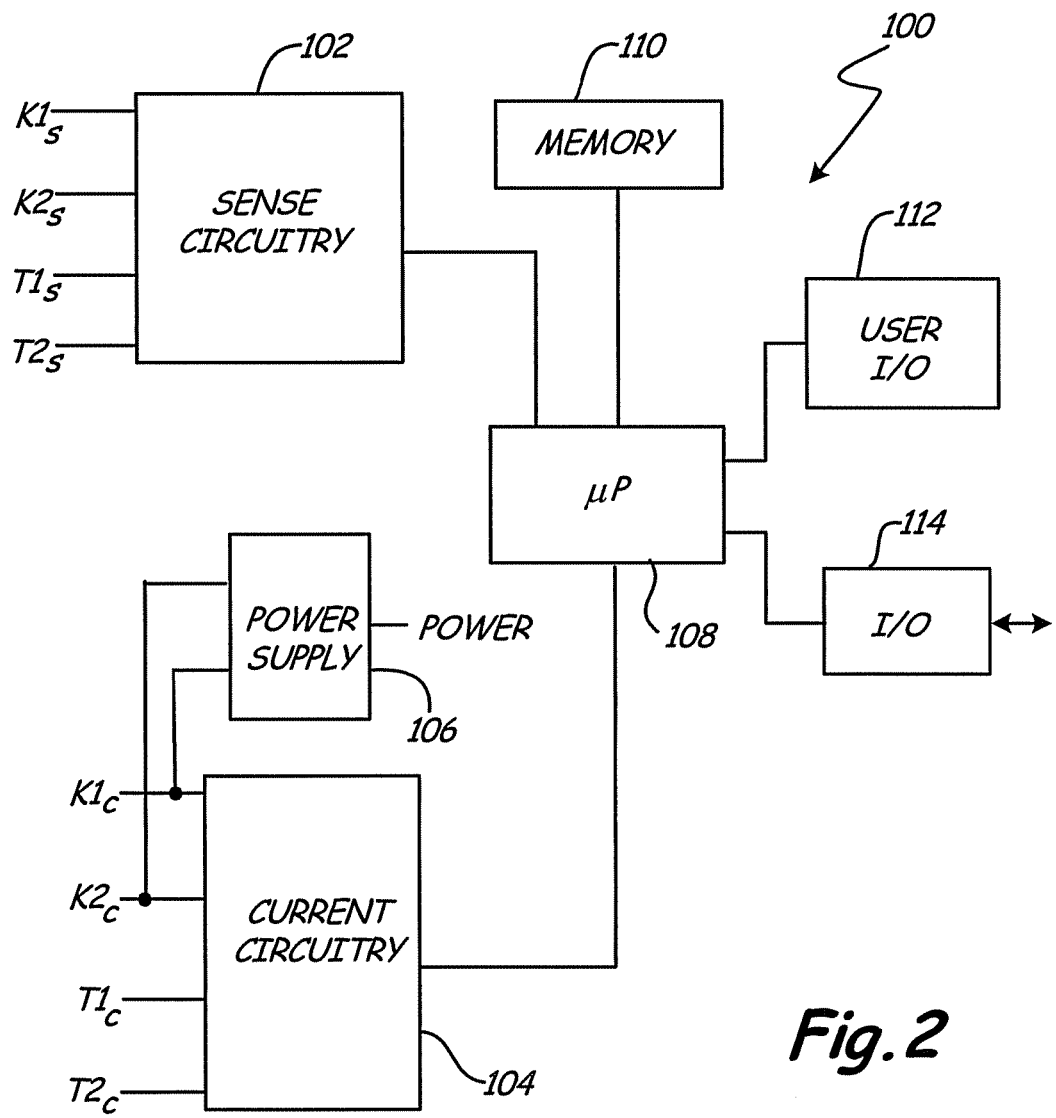
FIG. 2 is a simplified block diagram showing an automotive vehicle electrical system tester in accordance with one example embodiment of the present invention.

FIG. 2 is a simplified block diagram of automotive vehicle electrical system tester 100 in accordance with one example embodiment of the present invention. Tester 100 includes sense circuitry 102 which couples to connections K1$_S$, K2$_S$, T1$_S$ and T2$_S$. Similarly, tester 100 includes current drive circuitry 104 which connects to K1$_C$, K2$_C$, T1$_C$ and T2$_C$. Power supply circuitry 106 also couples to K1$_C$ and K2$_C$ and provides a power output which may be used for powering electrical components of tester 100. In another example embodiment, tester 100 includes a separate power source such as an internal battery. A microprocessor 108 couples to sense circuitry 102 and current circuitry 104 and operates in accordance with instructions stored in a memory 110. Memory 110 can include both volatile and non-volatile memory and may be used for permanently or temporarily storing information. User input/output circuitry 112 is shown coupled to microprocessor 108 and may include for example, button inputs, a display for output, audio inputs and outputs, etc. Such audio inputs or outputs can include a voice output or input, alarms, beepers, buzzers, etc. FIG. 2 also illustrates I/O circuitry 114 which can be optionally used by microprocessor 108 to communicate with any other type of device including network communications, other diagnostic components, centralized locations, printers, etc. In one example configuration, this includes a connection for coupling to the databus of the vehicle 12. For example, this could be an OBD II type databus.

The load 22 of the vehicle can be any type of load including loads which draw high current levels, for example, a starter motor, a magnetic switch, a ground connection, wiring harness, a terminal which may be susceptible to corrosion, a connection through a bolt which may have inappropriate torque or otherwise provide a poor connection, data carrying wires, sensor wiring, trailer wiring, etc. The invention is applicable to all wire sizes including small, medium and large gauge and is not limited to those discussed herein. In one example embodiment, the output is related to a particular current draw through the cabling. For example, the output can comprise an indication that there is a 0.5 volt drop through the cable when carrying a 500 amp current. Such parameter can also be used, for example, in a pass/fail test, i.e., if the voltage drop is more than a particular threshold at a given current level, a failure indication can be provided as an output. In one embodiment, the measured parameters comprise dynamic parameters such as dynamic conductance. However, any dynamic parameter can be used in accordance with the present invention including dynamic resistance, reactance, impedance, conductance, susceptance, and/or admittance, including any combination of these parameters, or others.

Figure 3A:
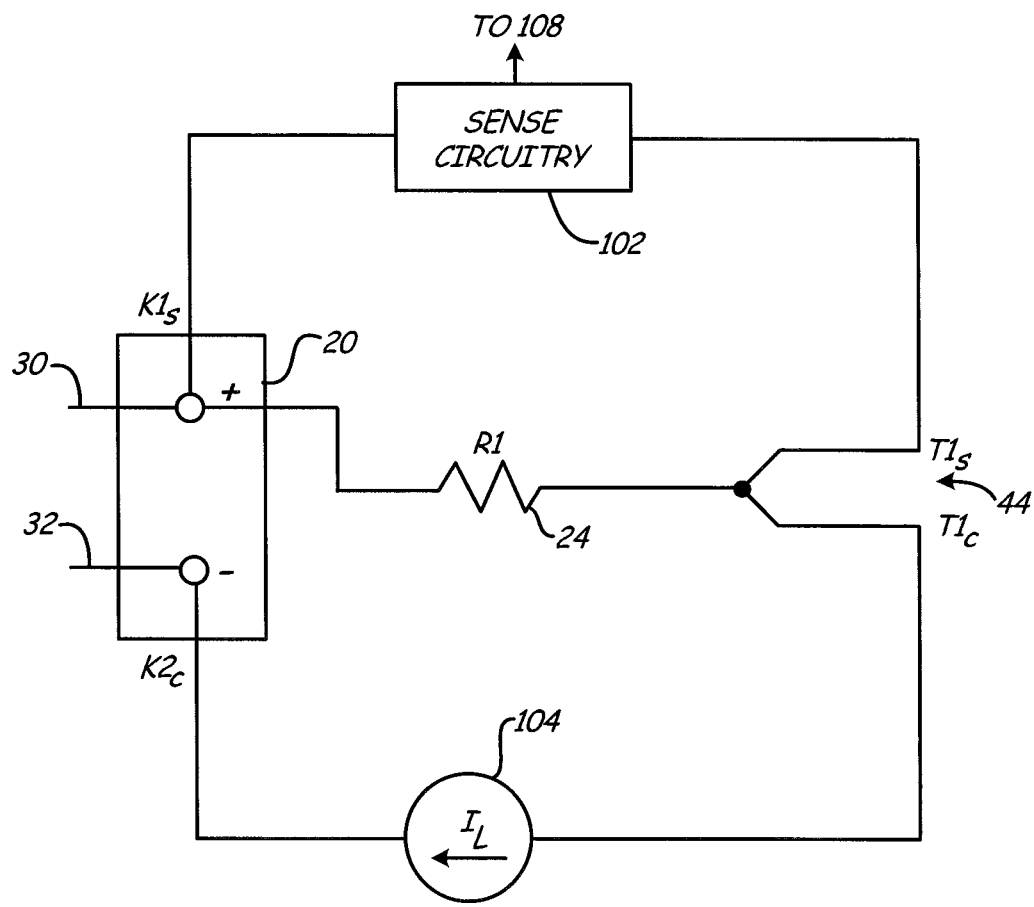
FIG. 3A is a simplified electrical diagram showing a configuration of circuitry for measuring a parameter of a wire of the vehicle.

FIG. 3A is a simplified block diagram showing the electrical connections to wiring 24 for measurement of resistance R$_1$. As illustrated in FIG. 3A, a current I$_L$ is applied by current source 104 through resistance R$_1$ of cable 24. The current I$_L$ flows through a current path from the positive terminal 30 of battery 20, through cable 24 and resistance R$_1$, and into test connector current connection T1$_C$ of test connector 44. The current source 104 provides a path for current from T1$_C$ to the K2$_C$ connection of Kelvin connector 42. This, as illustrated in FIG. 3A, couples to the negative terminal 32 of battery 20. The current source 104 can be an active or passive current source. For example, current source 104 may be a resistive load which operates under the control of microprocessor 108. Sense circuitry 102 is coupled across resistance R$_1$ using the K1$_S$ sense connection of Kelvin connector 40 and the T1$_S$ sense connection of test connector 44. Note that as discussed herein, the test connections 44 and 46 are illustrated as Kelvin connections, however the invention is not limited to this configuration.

Figure 3B:
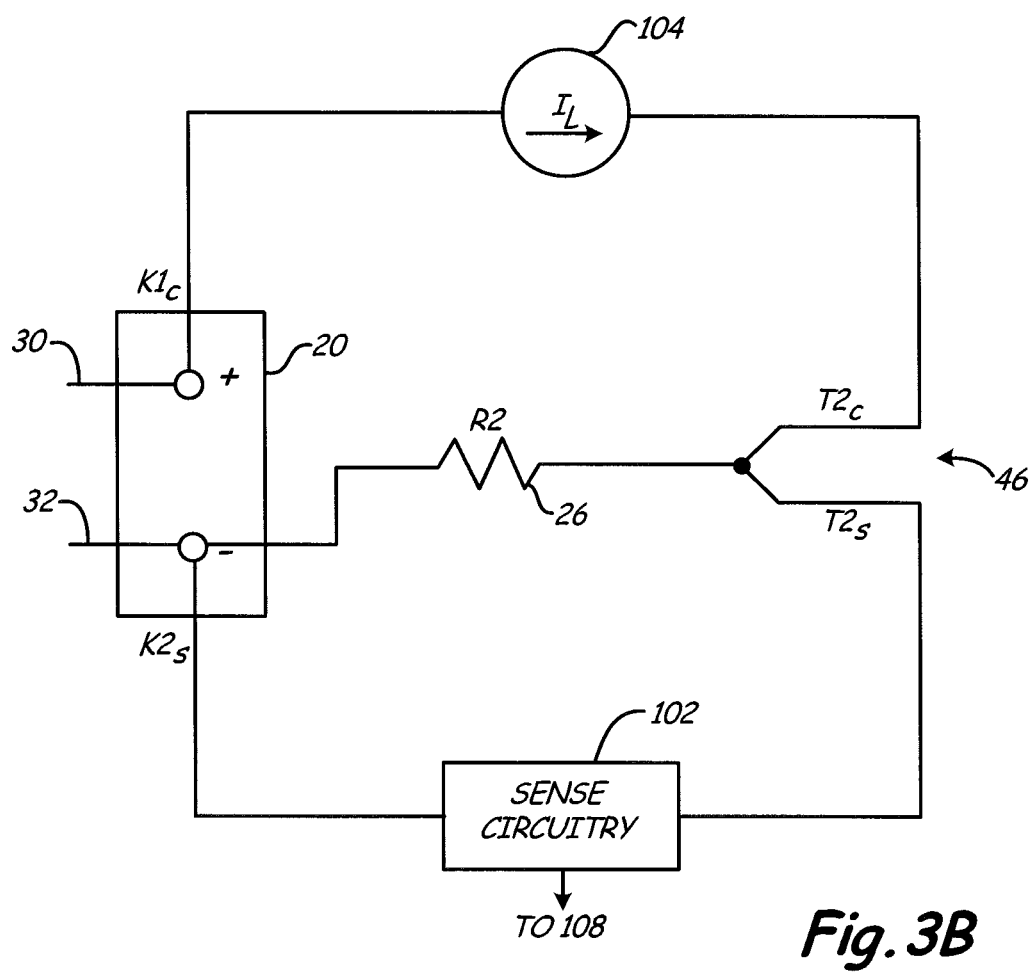
FIG. 3B is a simplified electrical diagram showing a configuration of circuitry for testing another wire of the vehicle.

FIG. 3B is a simplified block diagram showing a similar arrangement used to measure the resistance R$_2$ of cable 26. In FIG. 3B, a current I$_L$ is applied to resistance R$_2$ using current source 104 along with connection K1$_C$ of Kelvin connector 40 which couples to the positive terminal 30 of battery 20 and test connection T2$_C$ of test connector 46. A sense connection for sense circuitry 102 is provided by connector K2$_S$ of Kelvin connector 42 coupled to the negative terminal 32 of battery 20 along with the connector T2$_S$ of test connector 46.

Figure 4:
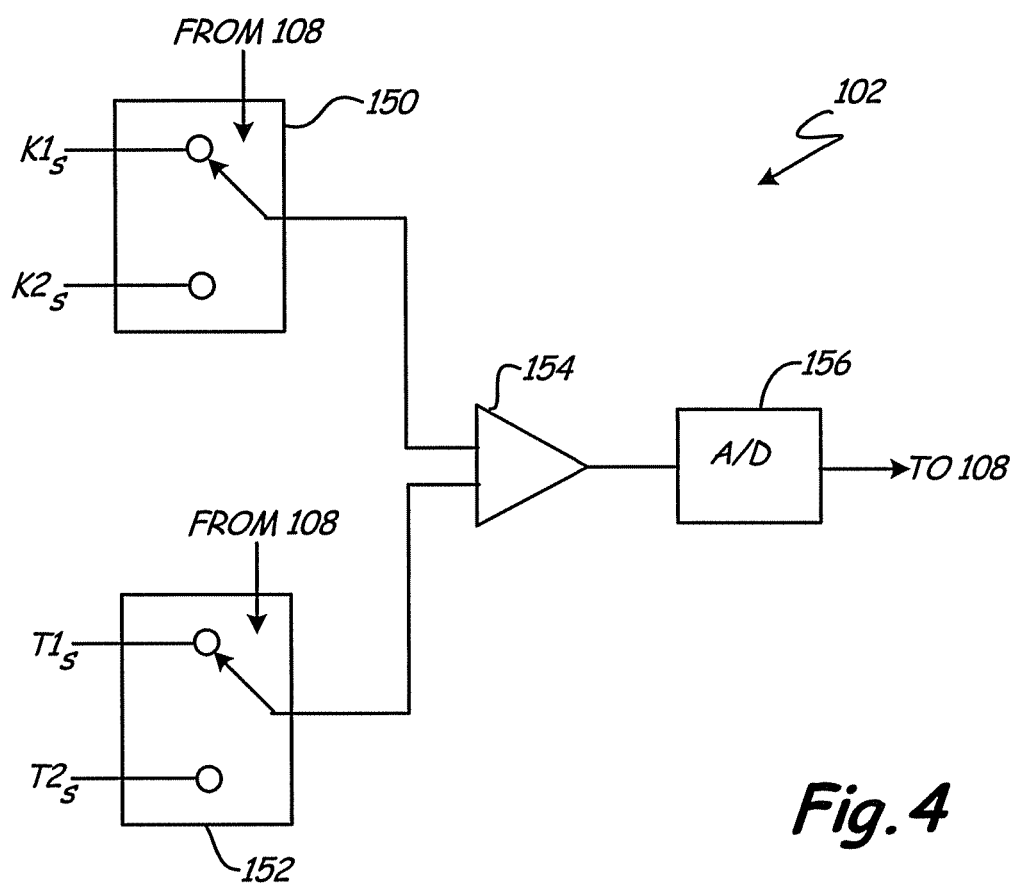
FIG. 4 is a simplified block diagram showing sense circuitry for use with the tester of FIG. 2.

FIG. 4 is simplified diagram showing one example configuration of sense circuitry 102. As illustrated in FIG. 4, sense circuitry 102 includes a multiplexor 150 operated under the control of microprocessor 108 which couples to the Kelvin sense connections K1$_S$ and K2$_S$. Multiplexor 150 is used to selectively couple one of the sense connections K1$_S$ and K2$_S$ to a differential amplifier 154. Similarly, a second multiplexor 152 operates under the control of microprocessor 108 and operates to selectively couple of the test sense connections T1$_S$ and T2$_S$ to the differential amplifier 154. Differential amplifier provides an amplified differential output to an analog to digital converter 156 which digitizes the analog signal and provides a digital signal to microprocessor 108. In one example configuration, the gain of the differential amplifier 154 maybe adjusted by microprocessor 108 to selectively increase or decrease the sensitivity of the circuitry.

Figure 5:
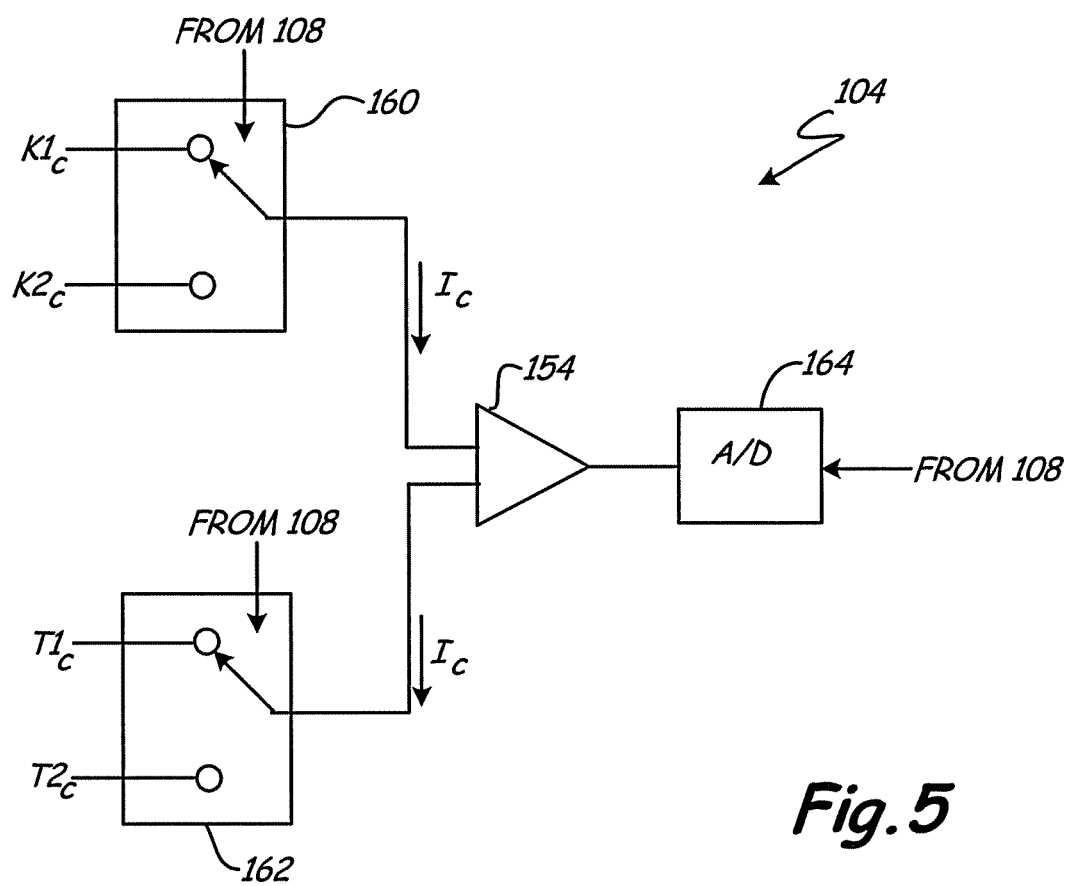
FIG. 5 is simplified block diagram showing current circuitry for use with the electrical system tester of FIG. 2.

FIG. 5 is a simplified block diagram showing one example embodiment of current circuitry 104 in greater detail. An embodiment illustrated in FIG. 5, a multiplexor 160 operates under the control of microprocessor 104 and selectively couples Kelvin connection K1$_C$ of Kelvin connector 40 or Kelvin connection K2$_C$ of Kelvin connector 42 to a current source 164. Similarly, a multiplexor 162 operates under the control of microprocessor 108 and selectively couples test current connection T1$_C$ of test connector 44 or test current connection T2$_C$ of test connector 46 to the current source 164. Current source 164 is coupled to microprocessor 108 and is controlled by microprocessor 108. Current source 164 may comprise, for example, a fixed resistance (in which case it is not necessary to connect current source 164 to microprocessor 108) or a plurality of selectable resistors or a variable resistance which provides a current path between one of the selected connectors coupled to multiplexor 160 and one of the connectors selected by multiplexor 162. In this configuration, the current source 164 is a passive current source formed by a resistance. However, an active current source may also be employed. Current 164 may also include current sense circuitry which is configured to measure a current I$_C$ flowing there through. This information can be provided to microprocessor 108 for use in determining the resistance of resistor R$_1$ or R$_2$ of cables 24 or 26, respectively.

During operation, microprocessor 108 shown in FIG. 2 controls operation of multiplexors 150, 152, 160 and 162 to arrange the test circuitry in the configuration illustrated in FIGS. 3A and 3B. The resistance being measured (R1 or R2) is calculated by microprocessor 108 using Ohms' law R=V/I where R is the resistance being measured, V is the voltage sensed by sense circuitry 102 and I is the current flowing through current circuitry 104. Operation by microprocessor 108 may be controlled by user I/O 112 shown in FIG. 2. For example, an operator may instruct the microprocessor 108 to initiate a measurement. In another example configuration, the operator instructs the microprocessor as to the amount of current I$_C$ to be applied during the test. This can be selected by the user, for example, based upon the type of wiring being measured, the specific use for the particular wiring being measured, the gauge of the wiring being measured, or other considerations as desired. The microprocessor 108 can provide an output, such as a pass/fail output by comparing the measured values with threshold levels. These threshold levels can be measured by a user through user I/O 112 and/or stored in memory 110. The particular thresholds may be changed based upon the particular test criteria being used. As discussed above, this could be based upon the particular wiring or cabling type, the use of which the wiring is applied, the gauge of the wiring, etc. Microprocessor 108 can also be configured to provide other information to the operator. For example, this includes any information which may be measured or otherwise retrieved by microprocessor 108 including voltage measures, maximum or minimum measurements, signal wave forms, user instructions or prompts, etc. In one example configuration, user I/O 112 may include an audible output such as voice prompting or verbal test results, or other sounds to instruct or provide information to an operator.

In one configuration, the user I/O 112 is used by an operator to instruct the microprocessor 108 as to the particular circuit configuration to be used as illustrated in FIGS. 3A and 3B. In another example configuration, for example, if a single test connector 44 or 46 is employed, microprocessor 108 measures a voltage using sense circuitry 102 between the test connection and Kelvin connectors 40 and/or 42. This measured voltage is used by microprocessor 108 to determine whether the test connector is coupled as showing by test connector 44 shown in FIG. 1 or if the test connector is coupled as shown by test connector 46 shown in FIG. 1. Based upon the measured voltage, microprocessor configures the circuitry in the proper configuration as illustrated in FIG. 3A or 3B.

Figure 6:
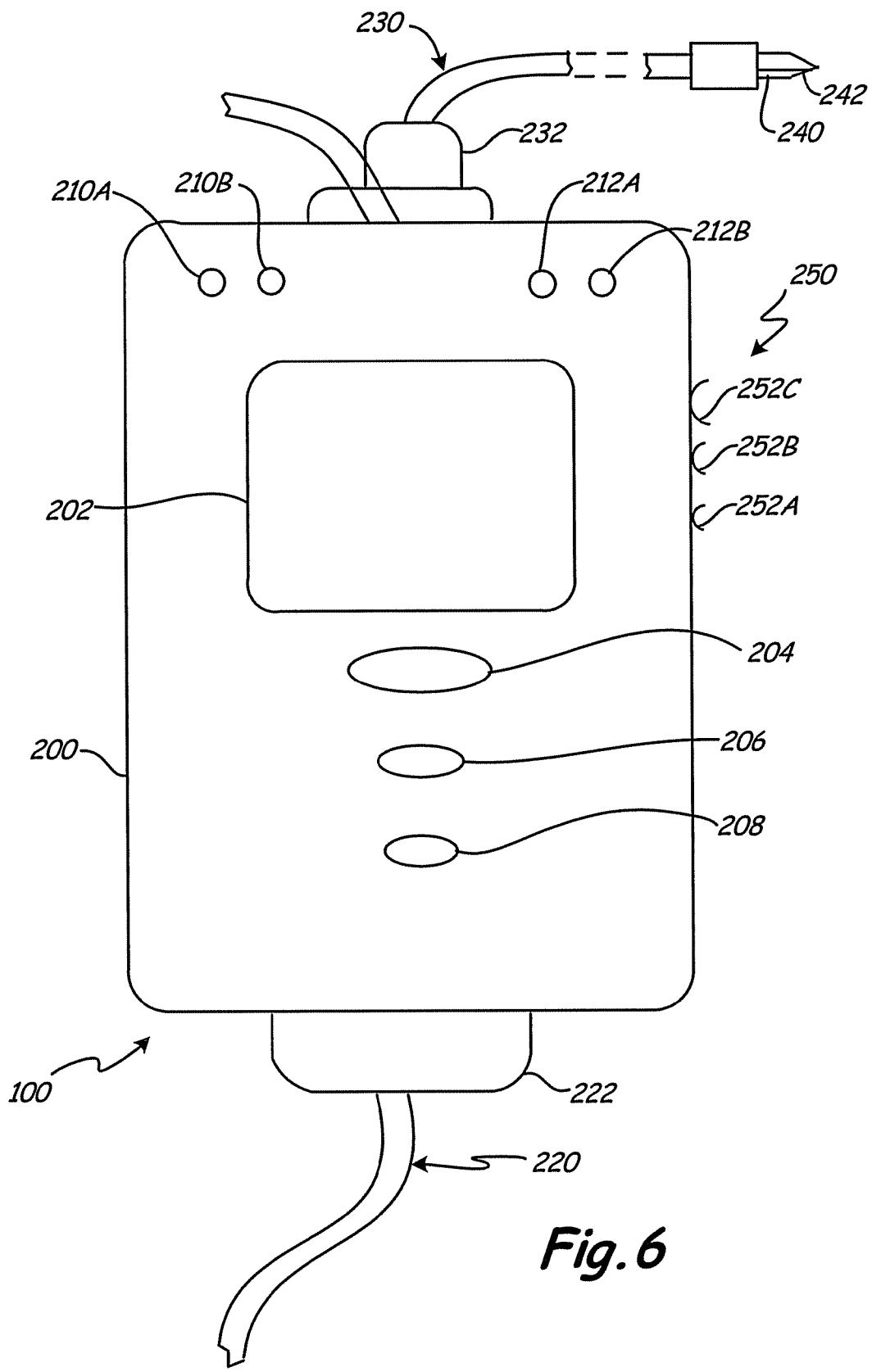
FIG. 6 is a front plan view of the electrical system tester of FIG. 2.

FIG. 6 is a plan view showing tester 100 which includes a housing 200 carrying a display 202 and user input buttons 204, 206 and 208. Display 202 and buttons 204-208 can comprise user I/O 112 shown in FIG. 2. Another example component of the user input/output 112 includes LED's 210A, 210B and 212A and 212B. A battery cable 220 couples to housing 200 to plug 222 and connects to Kelvin connectors 40 and 42 shown in FIG. 1. The Kelvin connectors 40 and 42 can comprise, for example, "alligator" type clamps for coupling to the terminals of battery 20. A test cable 230 couples to housing 200 to plug 232. In the example shown in FIG. 6, a distal end of test cable 230 comprises a piercing probe 242 configured to pierce through an insulation of a cable under test. Note that in such a configuration, the test connector, such as 44 or 46, may or may not be a Kelvin connection as illustrated in the above figures and may comprise a single connector. Some loss in accuracy may be expected however in some situations this may be acceptable. In another example configuration, the Kelvin connectors are provided through test cable 230 up to the distal end 240 of the test cable 230. At the distal end 240, the two Kelvin connectors are coupled together and a single connection is used for connecting to the cable under test. In yet another example configuration, the piercing probe 242 comprises two piercing probes such that a Kelvin connection is provided by piercing through the insulation of the cable. A piercing probe is not necessary and any type of test connection may be used including standard test probe configuration such as those available on volt meters, clamps, etc.

Button 204 can be configured as a "enter" button and buttons 206 and 208 can be configured as "up" and "down" buttons for scrolling through and selecting menu items displayed on display 202. For example, this can be used to also to receive information regarding the "gauge" of the wire under test. LED's 210A and 210B and 212A and 212B can be used to display test information. For example, when a wire of a positive polarity is detected either or both LED's 212A or 212B may be illuminated. Similarly, when test probe 242 is connected is to a wire of negative polarity, either or both of the LED 210A/210B may be illuminated. Button 204 can be used for initiate test button and cause the test to begin. Upon completion of the test, the microprocessor 108 can be configured to illuminate LED 210B or 212B if the test is successful. If the wire fails the test, LED 210A or 212A may be illuminated. In a similar configuration, an audio output can be provided, for example, a high pitch solid continuous tone to indicate a "good" wire, a "good" power wire, a high pitch beeping tone to indicate a "bad" wire power wire, a low pitch solid tone to indicate a "good" ground wire, and a low beeping tone to indicate a "bad" ground wire.

In another example configuration, a wire size gauge 250 is provided on the side of housing 200. In this example, the wire size gauge 250 provides three wire size gauges, 252A, 252B and 252C. These may be used by an operator to determine the gauge of the wire under test and input into the microprocessor 108 using user I/O 112. In another example configuration, wire size gauge 250 comprises an automatic gauge in which the wire under test is placed into a slot or the like and a sensor automatically determines the gauge of the wire and provides this information to microprocessor 108.

In one example configuration, a small gauge wire is tested with a current load of 1.25 amps, a medium gauge wire is tested with a current load of 2.5 amps, and a large gauge wire is tested with a current load of 5.0 amps, all with a fixed failure threshold of 0.2 volts. (i.e., if the measured voltage across the wire is greater than 0.2 volts, a failure is indicated). In another example embodiment, a fixed current load is provided and microprocessor 108 scales the measured result based upon the gauge of the wire.

Although the above description shows two different Kelvin connections to the battery terminals, in one configuration, Kelvin connections are not used and another example configuration, only a single Kelvin connection is used or no Kelvin connections are used. Similarly, only a single test connector may be employed and the invention does not require the two test connectors described above. Such an embodiment may be employed if desired, for example, to simultaneously measure the resistances of two separate wires. In a typical configuration, a single test connector will be employed. Similarly, the test connector may be a single connector and a Kelvin connection is not required. If a Kelvin connection is used, the Kelvin connection point can be configured anywhere along the test connector wiring and may be at a point that the test connector couples to the wiring of the vehicle, or at some other point in the wiring between the distal end of the test connector and the circuitry of the tester. The measurements may be made using static measurement techniques to obtain a static parameter or may be made using dynamic measurement techniques to obtain a dynamic parameter. Although the discussion above has generally referred to "resistance", the present invention is not limited to resistance and the parameter measured may be any parameter of the wire including those which have frequency dependent components. The tester may be powered with power from the battery of the electrical system or may contain an independent power source, for example, an internal battery. As discussed above, in some embodiments, Kelvin connections are provided to the terminals of the battery. In such a configuration, a parameter of the battery may be measured using the techniques discussed in the Background section, or other techniques.

The connection tip may be interchangeable and may be comprised a test probe, piercing tip, connector coupled to a particular type of electrical connection on the vehicle, or other configurations. As these tips are interchangeable, the overall resistance of the test connection may vary. Thus, in some configurations, the microprocessor 108 can be configured to implement a zeroing function whereby an operator can calibrate the measurement for the resistance of the wire based upon the selected probe tip. Such a configuration would typically not be required for a Kelvin connection. The zeroing function can be performed automatically by the microprocessor by measuring the resistance through the electrical connection, can be entered manually by an operator, may be selected by an operator scrolling through a table and selecting the probe in use. In such a configuration, memory 110 shown in FIG. 2 can contain information related to the resistance value for a particular probe.

In one configuration the measurement is presented to the operator in the form of "voltage drop at XX amps". However, the actual measurement may be performed at a current level other than that presented to the operator. If a small current is employed, conductance measurement techniques can be used to determine the voltage drop. If a current other than the displayed current is employed, the microprocessor 108 performs a scaling on the measurement. For example, if 5 amps is used to perform the measurement, the microprocessor 108 can compute the results of voltage drop at a different value such as 25 amps for display to the operator. This scaling can occur automatically, or can be selected by an operator. Such selection may be, for example, by scrolling through a utility menu presented to the operator using user I/O 110. In such a configuration, memory 110 can contain a scaling factor for use by the microprocessor 108.

In one embodiment, a relatively small current is employed. This reduces the amount of heat generated and reduces the power requirements of the testing device. The measurement can be performed using a dynamic forcing function such as a time varying current signal. For example, short pulses can be used if the device is not capable of sustaining a large current output for an extended period of time. In one example, a pulse width between 10 and 100 msec is used to perform the measurement.

The microprocessor can be configured to automatically sense the polarity of the connection. In such a configuration, the microprocessor sense the voltage measured and determines whether the probe is coupled to a power wire or to a ground wire and the appropriate load is applied. For example, if zero volts is sensed, the wire being tested is most likely a ground wire. Similar, if twelve volts is sensed, the wire being tested is most likely used to supply power. However, in some example configurations, a zero voltage reading may also indicate that the wire being tested is not connected. Similarly, a twelve volt reading may not be a power supplying wire if, for example, the alternator of the vehicle is generating a fifteen volt output. One example configuration to address this concern is to bias the probe tip to a voltage level. For example, circuitry within component 104 (or 102) can be provided to bias the probe tip to a value somewhere between the voltage at the two power leads coupled to the battery 20. When the probe tip is then coupled to the vehicle, the voltage at the probe tip will be pulled to either a more negative or positive value. Microprocessor 108 can sense this voltage and make a determination as to whether the probe is connected to a power lead or a ground lead. For example, if the probe tip voltage is within a predetermined voltage level from electrical ground, microprocessor can determine that the probe is connected to a ground connection. Similarly, if the probe tip is pulled within a predetermined voltage level from the plus connection of the battery, a microprocessor 108 can determine that a power lead is under test. In one example, the predetermined voltage is one volt which is advantageous if a protective diode is employed in the lead which would provide a voltage drop of 0.6 volts.

In one configuration, the tester 100 is configured to test an electrical connection in a wiring harness of an automotive vehicle. For example, referring to FIG. 1, element 22 can comprise the sensor of a vehicle, such as a sensor used to sense a condition of an engine or component of the vehicle. Similarly, element 22 can comprise a control element of the vehicle, such as an element used to control operation of the vehicle engine or drive system, convenience accessories, etc. In such a configuration, the wiring 24 may be part of a large bundle of wires (i.e., a wiring harness) whereby it is difficult to identify ends of a particular wire under test. When performing such tests, other connectors, for example, illustrated in FIG. 1, can be coupled to the vehicle power supply such as the battery and/or electrical ground. In such a configuration, the current circuitry 104 is configured to inject a tone signal having an AC component into the wire 24. This AC component may have a frequency in the audible range such that the sense circuitry 102 can be used to identify an opposite end of the wire 24. For example, the second connection can act as a probe (see 240 in FIG. 6) which, when placed in proximity of the wire will receive the tone signal. The sense circuitry 102 can be coupled to an audio output, for example user I/O 112, such that an operator can identify the selected wire by listening to a tone from the audio output. The volume of the tone will increase as the probe is placed in closer proximity to the selected wire and reach a maximum when the selected wire is touched by the probe.

Once the correct ends of the wire have been connected to the circuitry, the microprocessor 108 performs tests on the selected wire. Such tests include determining the current load capacity of the wire, identifying electrical short circuits or leakage to other wires, identifying leakage to electrical ground or power sources, testing the load carrying capacity of the wire for DC or AC signals including signals of different frequencies, etc. These tests can be performed for both AC and DC signals. For example, although a particular wiring connection may be capable of carrying a DC signal, AC signals (such as those used for data transmission, etc.) may be significantly degraded through the wiring due to stray inductance or capacitance. These tests can be performed by disconnecting both ends of the wire 24.

An operator can be prompted by the microprocessor 108 to perform the particular steps required for such a test. A memory 110 can be configured to contain a database of information related to the proper characteristics for wires used to connect to different types of systems. For example, data transmission wires may have one set of requirements whereas wiring used to connect to an analog sensor may have a different set of requirements. In such a configuration, the operator can scroll through a list of components and select the proper component for the particular wire being tested.

Although the present invention has been described with reference to preferred embodiments, workers skilled in the art will recognize that changes may be made in form and detail without departing from the spirit and scope of the invention. The measurements can be taken using multiple connections to the electrical system or by moving a single pair of connections to various positions on the electrical system. An output can be provided to instruct the operator where to place the connections.

What is claimed is:

1. A vehicle electrical system tester for testing the electrical system of a vehicle, the electrical system having a wiring harness which extends between electrical components of the vehicle, the wiring harness including a plurality of wires, the vehicle electrical system tester configured to measure an electrical parameter of at least one of the plurality of wires and comprising:

a first Kelvin connection having a current connection and a sense connection, the first Kelvin connection configured to couple to a first end of the at least one of the plurality of wires of the wiring harness;

a second Kelvin connection having a current connection and a sense connection, the second Kelvin connection configured to couple to a second end of the at least one of the plurality of wires of the wiring harness; and test circuitry coupled to the first Kelvin connection and the second Kelvin connection, the test circuitry applying an electrical signal between the first and second ends of the at least one of the plurality of wires through the current connection of the first Kelvin connection and the current connection of the second Kelvin connection, responsively measuring the electrical parameter of the at least one of the plurality of wires of the wiring harness using the sense connection of the first Kelvin connection and the sense connection of the second Kelvin connection and provides an output to a user related to a load carrying ability of the at least one of the plurality of wires which is determined based upon the measured parameter.

2. The vehicle electrical system tester of claim 1 wherein the measured parameter is based upon a measurement made through a connection to a battery of the vehicle.

3. The vehicle electrical system tester of claim 1 including an electrical connection to a battery of the vehicle and wherein circuitry of the vehicle system electrical tester is powered with power from the battery.

4. The vehicle electrical system tester of claim 1 wherein the test circuitry is further configured to provide an output to an operator, the output to the operator assisting the operator in identifying the second end of the at least one of the plurality of wires of the wiring harness.

5. The vehicle electrical system tester of claim 4 wherein the output comprises a tone.

6. The vehicle electrical system tester of claim 5 wherein the test circuitry applies a tone signal to the first end of the wire and the tone signal is received by the second Kelvin connection.

7. The vehicle electrical system tester of claim 1 including an input coupled to the microprocessor configured to receive information from an operator related to at least one of the components of the vehicle coupled to the first end of the at least one of the plurality of wires of the wiring harness.

8. The vehicle electrical system tester of claim 7 including a user output displaying a plurality of vehicle components and wherein the operator selects a vehicle component coupled to one end of the at least one of the plurality of wires of the wiring harness from the plurality of components through a user input.

9. The vehicle electrical system tester of claim 1 wherein the signal comprises a DC signal.

10. The vehicle electrical system tester of claim 1 wherein the signal comprises a AC signal.

11. The vehicle electrical system tester of claim 1 wherein the parameter relates to the ability of the at least one of the plurality of wires to carry digital data.

12. The vehicle electrical system tester of claim 1 including a user output and wherein the test circuitry prompts an operator to disconnect at least one end of the plurality of wires from the vehicle electrical system through a user output.

13. The vehicle electrical system tester of claim 1 wherein the second Kelvin connection comprises a piercing probe configured to pierce insulation of the at least one of the plurality of wires.

14. The vehicle electrical system tester of claim 1 including a user input coupled to the test circuitry.

15. The vehicle electrical system tester of claim 14 when the user input is configured to receive information related to a gauge of the at least one of the plurality of wires.

16. The vehicle electrical system tester of claim 1 wherein the test circuitry provides an output in the form of "voltage drop at XX amps".

17. The vehicle electrical system tester of claim 1 wherein the test circuitry provides an output related to electrical parameter of the at least one of the plurality of wires and a scaling factor.

18. The vehicle electrical system tester of claim 1 wherein the electrical parameter of the at least one of the plurality of wires comprises a dynamic parameter.

19. A method of testing wiring of an electrical system of a vehicle, the wiring including a wiring harness which extends between electrical components of the vehicle, the wiring harness including a plurality of wires, the method comprising:

coupling test circuitry to one end of at least one of the plurality of wires in the wiring harness using a first Kelvin connection, the first Kelvin connection comprising a current connection and a sense connection;

coupling the test circuitry to a second end of the at least one of the plurality of wires of the wiring harness using a second Kelvin connection, the second Kelvin connection comprising a current connection and a sense connection;

applying a signal with the test circuitry between the first and second ends of the at least one of the plurality of wires of the wiring harness through the current connection of the first Kelvin connection and the current connection of the second Kelvin connection;

measuring a parameter of the at least one of the plurality of wires of the wiring harness with the test circuitry using the sense connection of the first Kelvin connection and the sense connection of the second Kelvin connection; and provides an output to a user related to a load carrying ability of the at least one of the plurality of wires which is determined based upon the measured parameter.

20. The method of claim 19 including connecting to a battery of the vehicle and wherein the measured parameter is based upon a measurement made through a connection to the battery.

21. The method of claim 19 including providing an output to an operator, the output to the operator assisting the operator in identifying the second end of the at least one of the plurality of wires.

22. The method of claim 19 wherein the output comprises a tone.

23. The method of claim 20 including applying a tone signal to the first end of the at least one of the plurality of wires and receiving the tone signal with a probe proximate the second end of the at least one of the plurality of wires.

24. The method of claim 19 including receiving an input from an operator related to at least one of the components of the vehicle coupled to the first end of the at least one of the plurality of wires of the wiring harness.

25. The method of claim 24 including displaying a plurality of vehicle components on a display and wherein the operator selects a vehicle component coupled to one end of the at least one of the plurality of wires from the plurality of components.

26. The vehicle electrical system tester of claim 1 wherein the test performed on the at least one of the plurality of wires comprises a AC or a DC load capacity test.

27. The vehicle electrical system tester of claim 1 wherein the test performed on the at least one of the plurality of wires comprises detecting an electrical short circuit.

28. The vehicle electrical system tester of claim 1 wherein the test performed on the at least one of the plurality of wires comprises detecting leakage.

29. The vehicle electrical system tester of claim 1 wherein the microprocessor identifies the at least one of the plurality of wires based upon a voltage level bias applied to the first Kelvin connection.

30. The vehicle electrical system tester of claim 29 wherein the microprocessor identifies a power lead or a ground lead based upon the voltage level bias.

31. The vehicle electrical system tester of claim 1, wherein the first Kelvin connection is coupled to a battery and the second Kelvin connection is coupled to a load of the vehicle.

32. The vehicle electrical system tester of claim 1, further comprising a third Kelvin connection and a fourth Kelvin connection, wherein the third Kelvin connection is coupled to a battery and the fourth Kelvin connection is coupled to a load of the vehicle.

\* \* \* \* \*